(12) United States Patent
Salvati et al.

(10) Patent No.: US 6,393,431 B1
(45) Date of Patent: May 21, 2002

(54) COMPACT IMAGING INSTRUMENT SYSTEM

(75) Inventors: Jon R. Salvati, Skaneateles; David G. Perkins, Syracuse; Stephen C. Wilson, East Syracuse, all of NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 09/221,795

(22) Filed: Dec. 28, 1998

Related U.S. Application Data

(63) Continuation-in-part of application No. 09/052,570, filed on Mar. 31, 1998, now Pat. No. 6,106,457.
(60) Provisional application No. 60/043,374, filed on Apr. 4, 1997, and provisional application No. 60/075,406, filed on Feb. 20, 1998.

(51) Int. Cl.⁷ .............................................. G06F 17/30
(52) U.S. Cl. ........................ 707/104.1; 707/1; 707/10; 707/101
(58) Field of Search .............................. 707/1, 104, 10, 707/101

(56) References Cited

U.S. PATENT DOCUMENTS

| | | |
|---|---|---|
| 4,007,491 A | 2/1977 | Bolick, Jr. et al. |
| 4,247,876 A | 1/1981 | Bolick, Jr. |
| 4,319,290 A | 3/1982 | Bolick, Jr. et al. |
| 4,343,039 A | 8/1982 | Smith, Jr. et al. |
| 4,488,274 A | 12/1984 | Plunkett, Jr. |
| 4,519,009 A | 5/1985 | Bolick, Jr. |
| 4,526,449 A | 7/1985 | Moore et al. |
| 4,947,245 A | 8/1990 | Ogawa et al. |
| 4,998,818 A | 3/1991 | Kugler |
| 5,239,984 A | 8/1993 | Cane |
| 5,363,839 A | 11/1994 | Lankford |
| 5,519,808 A | 5/1996 | Benton, Jr. et al. |
| 5,877,819 A | * 3/1999 | Branson ...................... 348/701 |
| 6,106,457 A | * 8/2000 | Perkins et al. ............... 600/175 |
| 6,128,002 A | * 10/2000 | Leiper ......................... 345/156 |

\* cited by examiner

*Primary Examiner*—Diane D. Mizrahi
(74) *Attorney, Agent, or Firm*—Wall Marjama & Bilinsk LLP

(57) ABSTRACT

An imaging instrument includes a compact hand-held housing having an electronic imaging element supported within a housing, and a plurality of interchangeable instrument heads separably attachable to the housing. Each of the instrument heads includes an optical system disposed in alignment with the electronic imaging element along an instrument viewing axis. Preferably, the instrument includes a controller with sufficient programmable logic to capture and store a plurality of imaging images which can be transferred along with audio and/or annotation data relating to a captured image. Corresponding video, control and audio data can be then transferred using a receiving cradle to a computer which contains software which organizes the stored data for further processing. In a preferred example, the audio files can be transcribed through a network utilizing voice recognition software.

21 Claims, 16 Drawing Sheets

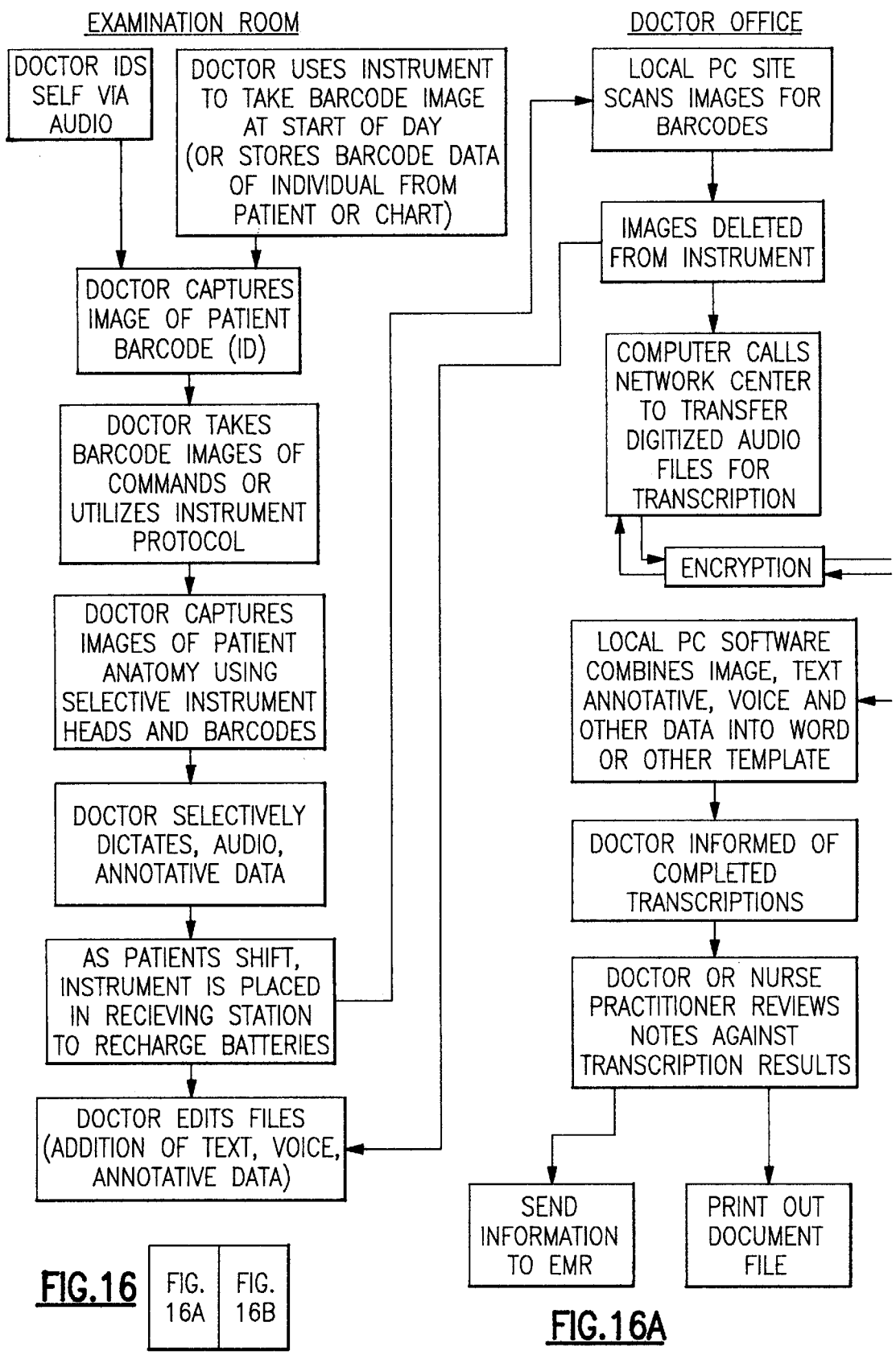

WelchAllyn

| | |
|---|---|
| PATIENT NAME: | MADELEINE PERKINS |
| PATIENT ID: | 314-15-9527 |
| PROVIDER NAME: | DR VITO LOSITO |
| EXAM DATE: | 3 FEBRUARY, 1998 |

DAVE PERKINS 8424

 1:15:56 PM  PATIENT COMPLAINED OF UNSIGHTLY BIRTH-MARK ON PALM OF RIGHT HAND. IT APPEARS TO BE A BENIGN HEMANGIOMA. NEWLY FORMED BLOOD VESSELS ARE READILY APPARENT IN THE BRIGHT, PROTRUDING AND SHARPLY DEMARCATED LESION. SINCE THE PATIENT HAS HAD FOR MANY YEARS, WE WILL EVALUATE IN SIX MONTHS.

WAVE SOUND
AUDIO 1:
2/3/98
1:15:56 PM
47 SECONDS

 1:43:30 PM  BP 126/86, P 82, Wt 190, HEENT: PERRLA, EOMS INTACT, TMs NL, OROPHARYNX BENIGN. NECK: SUPPLE W/O JVD, BRUITS, OR THYROMEGALY. CHEST: BS CLR TO PERCUSSION AND AUSCULTATION. HEART: WNL W/O GALLOP, MURMUR, RUB, CLICK OR IRREGULARITY. EXT: W/O EDEMA, PULSES INTACT.

WAVE SOUND
AUDIO 2:
2/3/98
1:15:56 PM
34 SECONDS

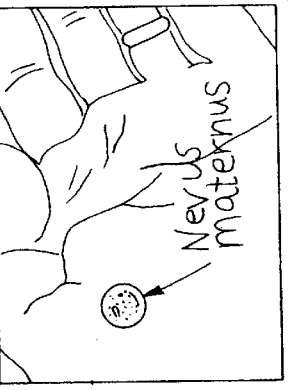

IMAGE 1: NEVUS MATERNUS LEFT HAND

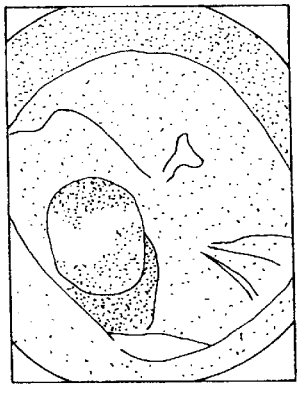

IMAGE 2: RIGHT TM, NORMAL

☒ APPROVED: *Dave Perkins* VITO LOSITO MD

FIG.18

COMPACT IMAGING INSTRUMENT SYSTEM

CROSS REFERENCE TO RELATED APPLICATIONS

This application is a continuation-in-part of U.S. Ser. No. 09/052,570 filed Mar. 31, 1998, now U.S. Pat. No. 6,106,457 which is based upon provisional applications Ser. No. 60/043,374 filed Apr. 4, 1997 and Ser. No. 60/075,406 filed Feb. 20, 1998.

FIELD OF THE INVENTION

This invention relates to the field of medical instrumentation, and in particular to a data management system utilizing at least one examination instrument capable of storing different forms of data. The system allows upload and download of captured data between the examination instrument(s) and a computer network to create and maintain records and reports.

BACKGROUND OF THE INVENTION

A number of hand-held diagnostic or examination instruments are known in the medical field for examining a patient, such as those commonly used during routine physician office visits. These instruments include, among others, skin surface microscopes which are used for diagnosing skin disorders, otoscopes permitting examination of the ear canal and tympanic membrane, and ophthalmoscopes for examining the eyes. Each of the above instruments have uniquely inherent features to allow an effective examination of the area of interest. Skin surface microscopes, for example, include a distal optical element having a relatively large diameter (e.g. approximately 15 mm) for direct placement onto a wart, lesion, or other skin disorder. Otoscopes, on the other hand, include a frusto-conical insertion portion having a relatively small diameter (4 mm) optic along with an overlaying safety speculum, which prevents insertion beyond a predetermined distance into the ear canal.

It has since become desirable for a patient to be able to witness a primary care or other examination along with the physician. Therefore, videoized versions of the above diagnostic instruments have been developed, such as those described in U.S. Pat. No. 5,363,839, issued to Lankford, U.S. Pat. No. 5,239,984, issued to Cane, et al, and U.S. Pat. No. 4,947,245, issued to Ogawa, et al. In each of the referenced instruments a miniature video camera, such as a CCD or other electronic sensor, is positioned either within the interior of the instrument or adjacently coupled thereto. The electronic sensor includes a light receiving surface or substrate which receives a focused optical image of a target of interest through a specifically designed viewing system, such as a rod lens, objective or other form of lens, typically positioned in the distal end of the instrument.

A separately disposed light box, or other source of illumination, provides white light through a sheathed cable which is tethered to the proximal end of the instrument. The cable includes an optical fiber bundle for directing the light specifically to the distal tip of the instrument, as well as electrical conductors for powering the electronic sensor. The electronic sensor, in turn, creates an analog or digital electrical signal which is remotely transmitted to a processor containing appropriate circuitry for then converting the transmitted electrical signal into a video monitor-ready (PAL, NTSC) format. The processed video signal is then separately displayed on a remote monitor. The use of videoized systems has become increasingly popular and has since taken on the term "telemedicine".

Telemedicine systems, like those described above, are quite expensive, with each system requiring a separate diagnostic instrument, along with dedicated cabling, light box, signal processor and video peripheral device(s). In addition, each system also requires a significant space allotment, posing a separate problem in that space is at a premium in physician's offices and other environments where such systems would be typically be used. It is therefore desirable to provide a telemedicine system which is capable of performing and displaying multiple forms of examinations.

It is another perceived desire in the field to make such telemedicine systems portable. In fact, it is highly desirous to allow examinations to take place outside the "normal doctor's office". Along with this need, is a similarly recognized need to allow portions of the system to be compactly arranged without the need for separate peripherals or connecting devices.

Improved organization of patient records is yet another current need in the medical field. To date, creation and maintenance of patient files has been largely a manually managed activity. Data which can form a part of the overall patient record, however, can take on a number of different forms. For example, it has been known that data can be accumulated in a umber of forms, particularly with the advent of telemedicine involving image capture, portions of which might form part of a patient chart or record.

In addition, physicians, such as family practitioners, surgeons, etc., invariably record notes during a patient visit and examination. In some instances, of course, the physician may write information directly into the patient's file. The usual practice, however, is to record events of an examination using a hand-held recording device. The taped notes are then later transcribed and then added to the patient's file. Throughout the course of a single day, however, it is possible that a physician may see as many as 40 patients. This kind of volume makes the task of compiling and transcribing notes difficult, or at a minimum time consuming, either for the physician or for the physician's staff. Reference is herein briefly made to FIG. 12 and 13, broadly depicting a transcription procedure in accordance with the prior art.

More particularly, and prior to a patient encounter, a patient chart is taken from the office files and given to the physician. The physician then examines the patient, adding his or her notes to the file and dictating as needed during the course of examination, typically using a hand-held tape recorder. The physician identifies the patient and adds a time and date stamp at the start of each dictation session. Usually, a single tape will contain dictation relating to a plurality of patient encounters over the course of a typical working day or shift. Often the dictation will be done at the end of the day, when details of the patient visit are sketchy. The doctor must usually rely upon memory, and whatever notes made during the course of examination. As noted, however, a doctor will often see many patients during the day, obscuring the details of a specific visit.

The tape is then sent to a transcriptionist, who listens to the tape, as best understood, and manually types the chart notes. The notes are either into typed into a computer record or onto paper for each patient record on the tape. In any event, a copy of the chart notes are then printed and forwarded to the physician for review. The physician fills in any data which could not be successfully interpreted by the transcriptionist, and otherwise edits the chart notes which are then typed in accordance with the corrections. After again reviewing the chart notes, as necessary, the physician signs off the transcribed record. The record is then added to the patient's file. The creation of patient records or reports incorporating several different types of data, including audio and video data files, is even more difficult.

A number of potential problems can occur from the above procedure. First, if the tape(s) is faulty or lost, the physician will be required to create the chart records from memory and/or consultation of any written notes which may have been taken during the examination. A similar problem occurs if the tape is prematurely and accidentally erased. The audio tape is the primary source of information, which both the transcriptionist and the physician must rely upon for both creating the draft chart notes and for reviewing purposes. The end result is a heightened probability that the records will be incomplete or inaccurate.

In a similar vein, the printed notes could also be lost or misplaced, potentially delaying the reviewing process. Delays obviously will increase the probability that incorrect or incomplete records will be generated. If known video diagnostic instruments such as those shown in FIG. 1 are used, the data obtained from each must also be labeled and separately attached to the file. Based on the amount of time taken, it could be difficult to correctly place this data with the transcribed data, if any. As should be apparent, a myriad of different combinations using various types of data are possible.

To date, though there are known transcripting apparatus available, none conveniently combine audio data with other forms of collected data, such as captured images, sketches by the physician, or other patient or related data obtained from other instruments to be retained and used in compiling and assembling complete examination records which can then be effectively stored and maintained.

SUMMARY OF THE INVENTION

Accordingly, it is a primary object of the present invention is to improve the present state of the art of medical examination systems.

It is yet another primary object of the present invention to provide a data management system, for medical or other records, such as inspection, quality control, inventory, etc. using an instrument which is capable of capturing and storing multiple forms of data input. This data can then be effectively transferred into a central network capable of linking the data into accumulated data records which can be updated and maintained automatically.

Yet another primary object of the present invention is to provide an instrument capable of storing various forms of data (i.e.: a multimedia instrument), that can be adaptively interconnected with a plurality of output devices to allow transfer and subsequent processing of a plurality of stored data inputs.

It is yet another primary object of the present invention to provide a medical records (data) management system in which a plurality of captured audio files can be subsequently transferred and transcribed remotely. The transcribed results can then be transferred directly into a patient record along with other data forms relating to a specific patent encounter. The entirety of the data can be stored and/or output into a convenient format which can be printed and added to a patient file.

Therefore and according to a preferred aspect of the present invention, there is provided a method for creating and maintaining records containing at least image, audio data relating to a plurality of subjects using a hand-held multimedia examination instrument having means for capturing various forms of data, the method comprising the steps of:

capturing image data relating to at least one subject of interest using said hand-held multimedia instrument;

capturing audio data corresponding to at least one subject of interest using said multimedia instrument;

capturing control data relating to said at least one subject of interest using said multimedia instrument;

transferring the captured audio and image data from said multimedia instrument to a computer site;

storing said data in a database associated with said computer site;

transferring audio data from said computer site to a transcription site;

transcribing said audio data at said transcription site into text-readable data;

transferring said text-readable data to said computer database for storage; and incorporating said text-readable data with associated image data as part of a data record.

More preferably, the hand-held multimedia instrument is part of an overall data or records management system. According to a preferred embodiment, the instrument can be interconnected to a receiving cradle or docking station having means for allowing data transfer between the instrument and an external source to allow transfer of audio, video and other data files stored in the instrument or the external source which can, for example, be part of a single computer or computer network. In this manner, protocols, operating instructions, or data from other instruments can be transferred directly to the multimedia instrument according to one embodiment and data and the like can be transferred from the instrument.

In accordance with a preferred embodiment, data is transferred to an intermediate or local PC utilizing software which arranges the data into a scripted template, such as a patient chart of convenient architecture. The template includes allocation for voice, video, annotation and other data and can be stored in a local database. The local database, would for example, contain patient files for a specific physician's office.

In addition, the transferred voice or WAV files can be further transferred into a network including a data center (e.g. a server) utilizing a global database for tying in a plurality of similar multimedia or other suitable devices. According to a preferred embodiment, the data center can receive and extract a plurality of raw voice data files from a particular instrument, direct the files remotely for transcription and subsequently report all data of a patient encounter, including transcription or consultation data taken from voice inputs, back to the local physician in a suitable record format.

According to a preferred feature, the described data management system utilizes software capable of discriminating a captured video image from known 1D or 2D bar code symbology or for pattern recognizable data. This allows the multimedia instrument to tag data files automatically without requiring separate manual input from the user.

According to yet another preferred embodiment, the multimedia diagnostic instrument includes individual instrument heads, each head including separate and unique viewing optics which focus an optical image onto a contained electronic imager, the imager being preferably situated adjacent the front face of the instrument body.

According to yet another preferred aspect of the present invention, there is described a record management system comprising:

at least one examination instrument including a plurality of instrument heads, wherein at least one of said heads and said instrument body include an optical system for directing an image onto an electronic sensor disposed in said instrument and display means for displaying at least one directed image and data capture means for capturing audio and video data;

means for transferring data files from said instrument to a processing means, said processing means including means for transcribing notes from audio data contained in said files; and for accumulating data into a record format.

According to a preferred aspect, there is described a method for transcribing a plurality of record notes, comprising the steps of:

storing a plurality of data in several forms using a multimedia instrument, said instrument having digital camera means and display means contained therein, as well as means for taking audio data corresponding to a displayed video image;

transferring data from said instrument into a database;

extracting audio data from said transferred data;

moving the audio data files to a central processing station; and using voice recognition software to process the transcription notes, the software preferably being able to recognize and utilize learn technology based on a given voice being recognized for processing;

creating transcriptions which can be associated with a patient file having at least one video image attributed thereto.

An advantage of the present invention is that a telemedicine system is provided which allows multiple types of examination to be performed in a simple and efficient manner using a single instrument body and interchangeable instrument heads.

Another advantage of the present invention is that multiple instrument heads can be selectively and simply interchanged with a single instrument body to provide versatility and to provide the advantages of multiple videoized systems without a significant impact beyond that of a single dedicated system. Moreover, the instrument is portable, meaning that examinations are not confined to a dedicated location, such as a doctor's office.

Still another advantage of the present invention is that the described system allows multiple examinations to be performed in a space envelope which is smaller than conventionally known videoized systems. The instrument also includes an integral display and means for compactly storing a series of images, or of displaying real or stored images and playback of captured audio-related data. This capability allows the physician to more efficiently improve the capabilities of the office. In addition, the instrument is preferably linkable to a PC, a PC network or other peripherals capable of using data retrieved from the instrument. Yet, the physician or other user of the instrument can use the videoized instrument from literally any location without restriction, for example, to an office setting.

Still another advantage of the present system is that numerous types of data including imaging data, audio data, and annotation data can be easily stored, transferred, and utilized. This storage allows the creation of a "multimedia" data file and allows efficient creation and maintenance of records provided in a useful format which incorporates each data type within the confines of a specific record.

Yet another advantage is that the above described system can be easily adapted into a multimedia data management system. According to one specific example, a transcription service can be created allowing audio data captured and stored by the instrument(s) to be added into a computer network having voice processing software using a cradle or dictating station which is tied to a local PC which can be linked into the network. As a result, doctors can review records more quickly because the files incorporate image data, allowing the physician to recognize patients faster and recall particular conditions and physiology. An immediate benefit occurs when dictation occurs later after a number of separate patient encounters, and when transcribed notes are reviewed days later.

These and other objects, advantages, and features will be described in the following Detailed Description of the Invention which should be read in conjunction with accompanying drawings.

BRIEF DESCRIPTION OF THE DRAWINGS

FIG. 18 is a sample report created using the data management system of the present invention.

DETAILED DESCRIPTION OF THE INVENTION

The following discussion describes the present invention according to certain specific embodiments and more particularly to a physician's office environment. As will be apparent from the following discussion, however, there are many other modifications and variations which can be employed by those of skill in the field embodying the concepts which are described herein. For example, the above system could similarly be used in a hospital emergency room, HMO or other environment in which a plurality of patient encounters take place on a daily basis. In addition, and though the presently described embodiments relate specifically to the medical field, it will be readily apparent to one of sufficient skill in the field that other suitable fields utilizing numerous forms of data input and reporting for varying numbers of samples including, but not limited to manufacturing, quality control, inspection, engineering, and inventory can effectively utilize the inventive concepts presented herein.

Figure 1:
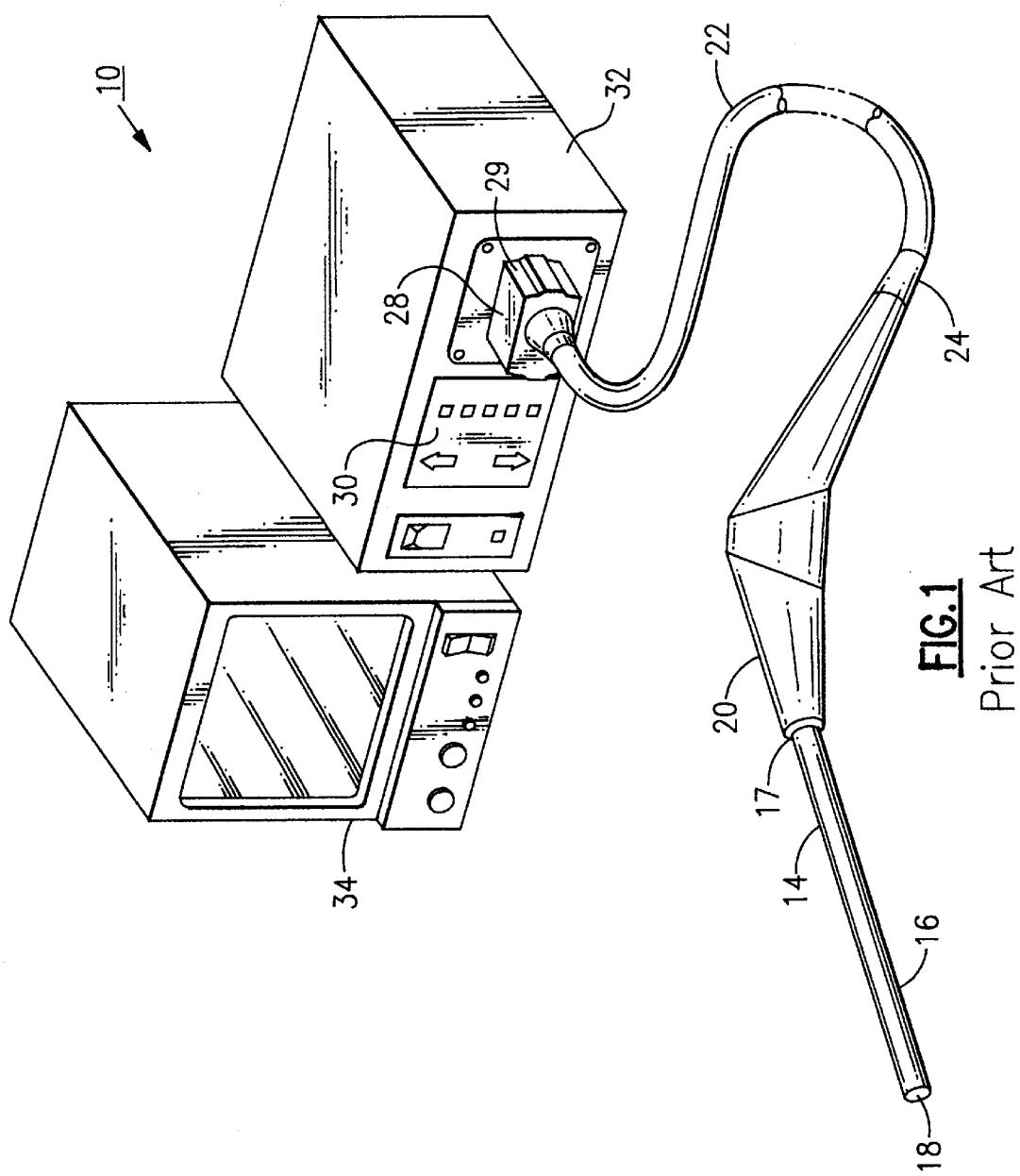
FIG. 1 is a front isometric view of a medical diagnostic instrument system in accordance with the prior art.

Turning to FIG. 1, there is shown a video medical diagnostic instrument system in accordance with the prior art. The instrument system 10 includes a medical diagnostic instrument 14, in this instance an endoscope (ie: a video laparoscope is shown) defined by an elongate instrument body 16 having a distal end 18 and an opposite proximal end 17 attached to a handle section 20. An electronic sensor or element (not shown), such as a CCD (charge coupled device), is disposed within the instrument body 16 and receives an optical image of a target of interest through an imaging system, such as a relay, objective or other known lens system (not shown) in a conventional manner. The electronic sensor includes support electronics which convert the optical signal into an electrical signal which is transmitted along a sheathed cable 22 depending from the proximal end 24 of the handle section 20.

According to the above-described system, a video processing module 28 forms the proximal end of the sheathed cable 22, the module containing processing electronics for converting the transmitted electrical signal into a video monitor-ready (PAL, NTSC, etc.) signal. The video processing module 28 is attached into a receiving cavity 29 of a light/power box 32 containing a high output light source, such as an arc lamp (not shown) or other source of white light. The light from the high-intensity light source is transmitted from the light box 32 through an optical fiber bundle (not shown) contained within the sheathed cable 22, and guided into the diagnostic instrument body 16 to the distal end 18 thereof. The light/power box 32 also serves to furnish power to the diagnostic instrument 14 through electrical connectors, also contained within the sheathed cable 22, the power/light box being operated by a control panel 30.

In use, a processed video signal of the target of interest is displayed by an interconnected video monitor 34 which is connected to the light/power box 32 to allow viewing, by a physician and patient(s). Other peripheral devices, (not shown) such as a video printer, a video tape recorder, a PC, etc., can also be substituted into the above described instrument system.

The above diagnostic instrument system 10 introduces a number of discrete components and requires a significant spatial footprint typically restricting the use of the system to a dedicated area, such as a physician's office, an emergency room, etc. Though the above laparoscopic system is dedicated to a particular target of surgical interest, (e.g., the abdominal cavity), other types of diagnostic instruments, such as otoscopes, colposcopes, and dermatoscopes, among others, are required for performing other types of examinations that are typically done during a patient visit. That is, it is not uncommon that a variety of different examinations, (ear, eye, throat, skin) be performed in a single family practitioner visit. The ability to electronically capture and archive images for each type of examination would be desirable, allowing the patient and the physician to both view a target of interest, but as noted above, typically a separate dedicated system is required for each instrument.

MULTIMEDIA DIAGNOSTIC INSTRUMENT

Figure 2:
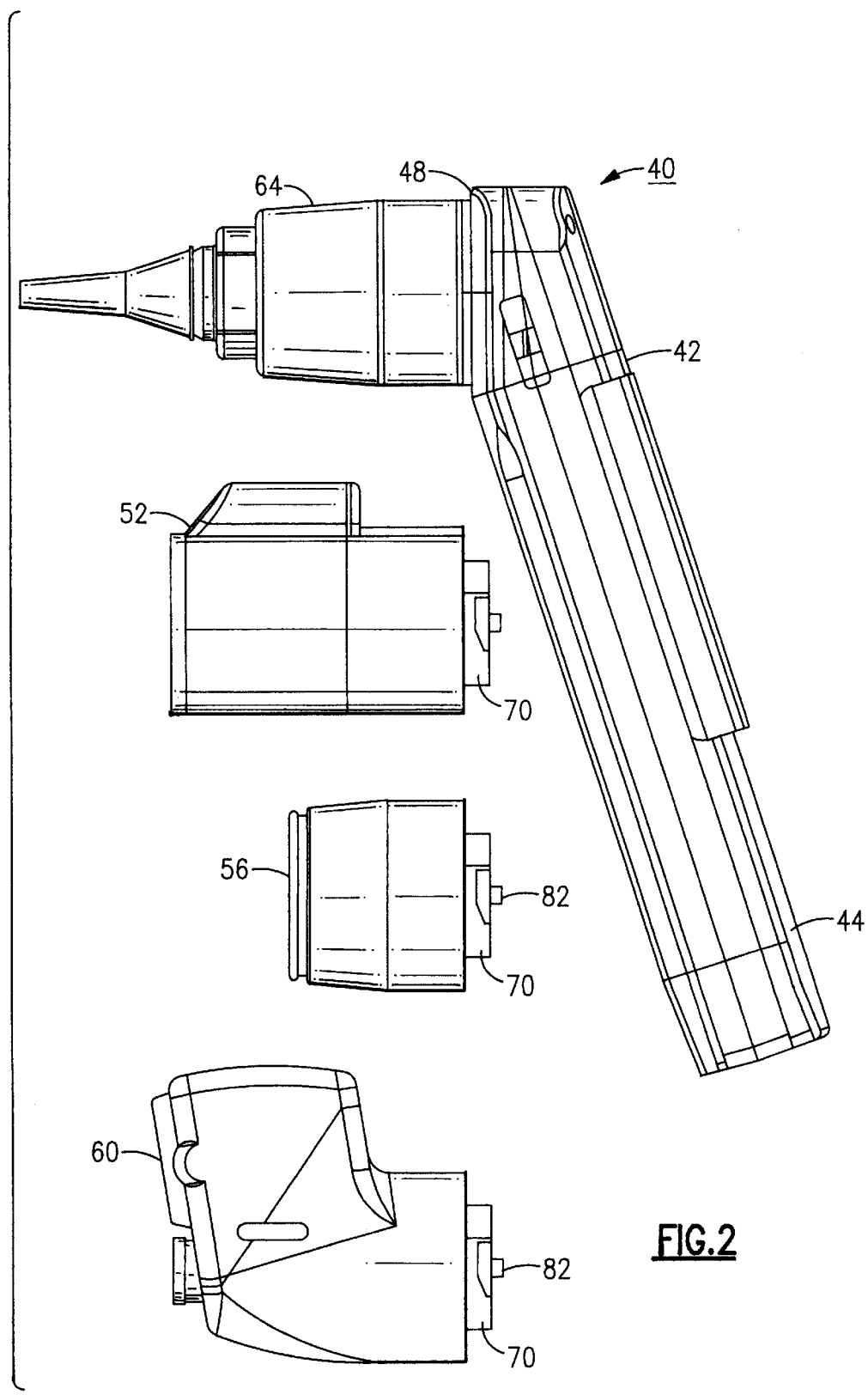
FIG. 2 is a side partial view of a multimedia examination instrument having interchangeable instrument heads made in accordance with a preferred embodiment of the present invention.

Referring now to FIG. 2, a diagnostic instrument system 40 according to a preferred embodiment of the present invention comprises a compact diagnostic instrument 42 including a housing or body 44 having a front interface 48 with means for allowing selective releasable attachment thereto of a plurality of instrument heads. According to this embodiment, the instrument heads include a general purpose instrument head 52, a dermatological instrument head 56, a high magnification instrument head 60, and an otological instrument head 64.

Other types of instrument heads, such as for ophthalmoscopic use and employing optical systems such as described in commonly assigned U.S. Pat. Nos. 4,526,449 and 4,998,818, for example, incorporated by reference herein, can also be utilized.

Figure 3:
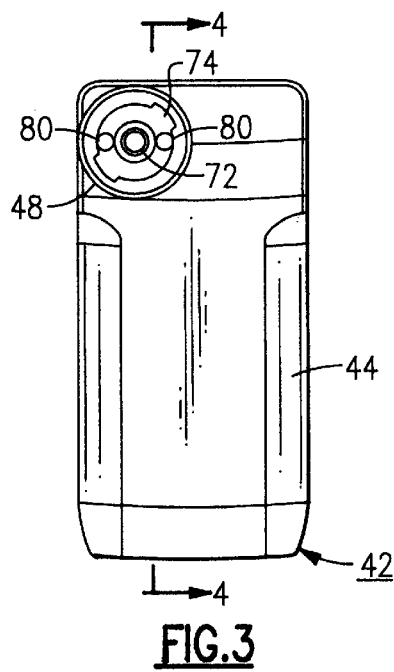
FIG. 3 is a front elevational view of the multimedia instrument of FIG. 2.
Figure 4:
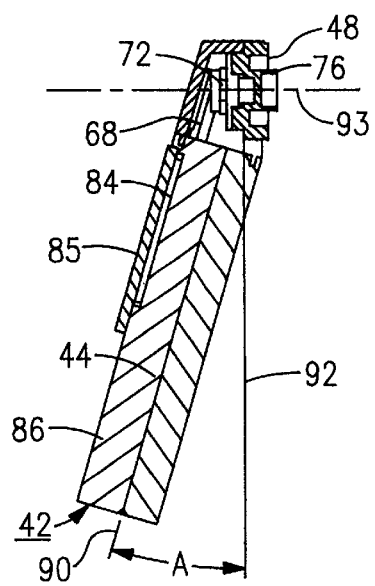
FIG. 4 is a side partially sectioned view of the multimedia instrument as taken through line 4—4 of FIG. 3.

In brief and referring to FIGS. 2–4, each of the instrument heads 52, 56, 60, and 64 include a latching member 70 which engages a cavity 74 provided in the front interface 48 to allow releasable engagement with the diagnostic instrument 42. Some or all of the latching members 70 include electrical contacts 82 which engage corresponding contacts 80 extending from the front interface 48 to power an illumination system contained in an instrument head. In addition, each of the instrument heads include unique optical systems to enable viewing of a target of interest when assembled. Specific details relating to the instrument heads and the latching mechanism are provided in U.S. Ser. No. 09/052,570, the entire contents of which are herein incorporated by reference.

Referring to FIGS. 3 and 4, the diagnostic instrument 42 for purposes of the described system 40, FIG. 2, is a compact hand-held digital camera having a defined interior 68, shown partially in FIG. 4. The interior 68 is appropriately sized to retain a plurality of components including an electronic imaging element 72, such as a charge coupled device (CCD) having related processing circuitry or CMOS having substantially all of the video processing disposed directly on the chip, disposed adjacent a window 76 or clear covering at the front interface 48 provided in the instrument housing 44.

Figure 8:
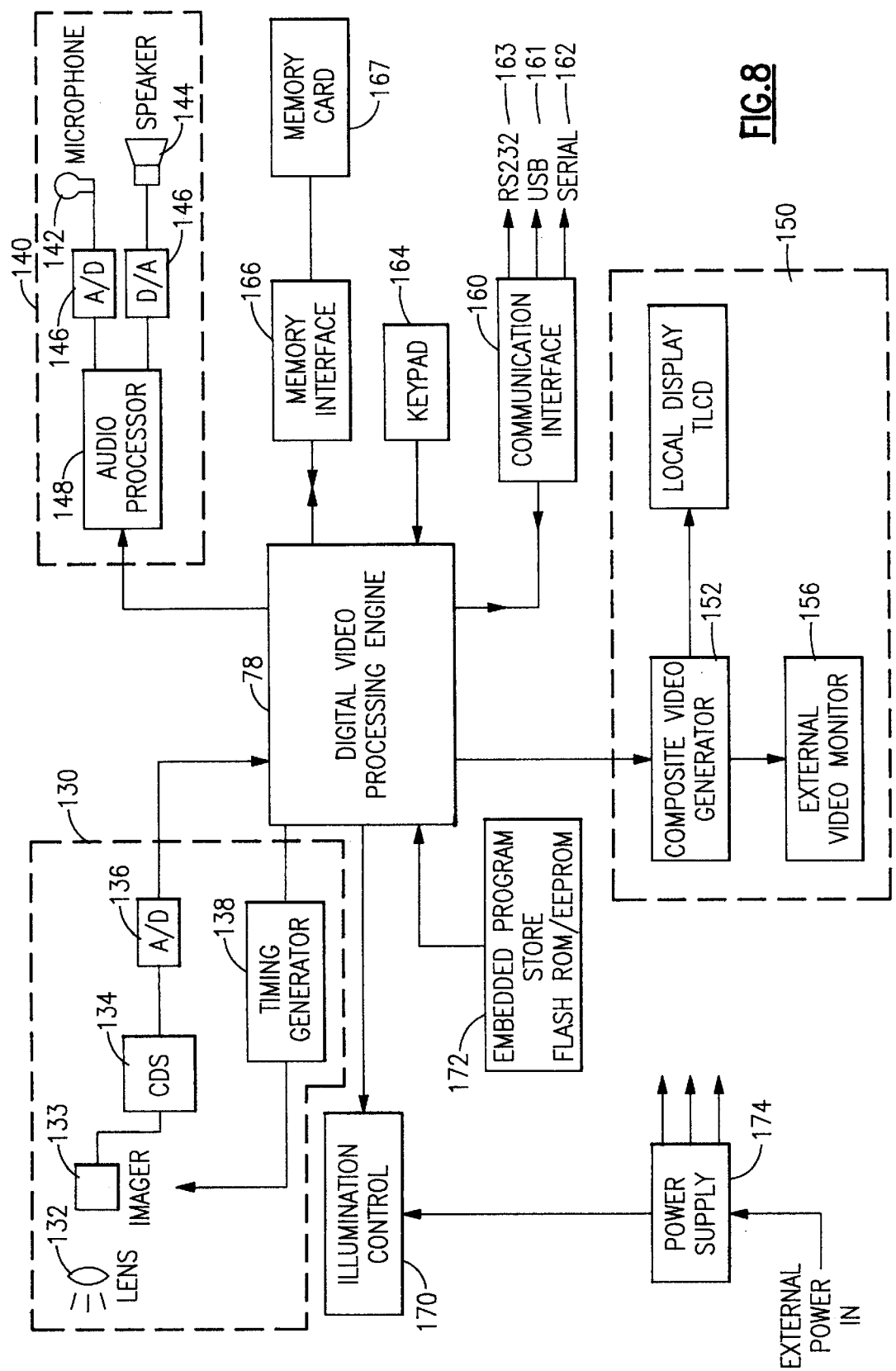
FIG. 8 is a block diagram of a preferred system architecture for a multimedia examination instrument in accordance with the present invention.

The instrument 42 further includes a controller, such as a digital video processing engine 78, FIG. 8, having sufficient memory and programmable logic contained within the interior 68 of the instrument housing 44 and interconnected to the retained components, including an integral touch-sensitive TFT liquid crystal display (LED) 84, provided on the rear side 86 thereof. Alternately, an eyepiece type of display, shown diagrammatically in FIG. 8, could be used. The processed digital video signal is outputted to the display 84 by a composite video generator 152, FIG. 8, for viewing by the user. A protective cover 85, slidingly attached to the rear side 86 of the housing 44 by known means, allows selective access to the display 84. Preferably, the rear side 86 of the instrument housing 44 is angled, as shown in FIG. 4 by reference numeral 90, relative to the vertical axis 92 and orthogonal to the viewing axis 93 of the instrument 42 to facilitate viewing of the display 84 for the user.

According to the embodiment, an angle, represented in FIG. 4 as -A-, of approximately 15 degrees is suitable.

Figure 6:
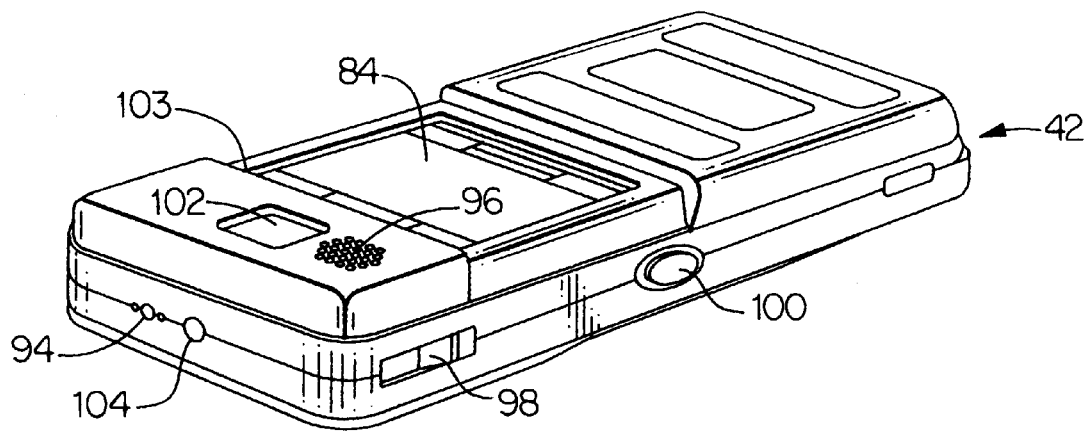
FIG. 6 is a side perspective view of the instrument of FIG. 5, showing the sliding cover being moved to an open position to reveal a touch sensitive display.

Referring to FIGS. 2, and 6, the architecture of the digital video processing engine 78, FIG. 8, allows various forms of data to be captured and stored in conjunction with image (video) information. An internal condenser microphone 94 disposed on the top exterior of the instrument housing 44 allows audio information to be captured and stored selectively into the buffer memory of an audio processor 148, while an integral speaker 96 disposed on the rear side 86 allows playback of the stored audio information in conjunction with a stored video image. Audio data that has been captured in the internal buffer of the audio processor 148 is transferred to the digital video processing engine 78, which appends the audio data to an electronic file containing the desired image and annotation data, along with control data. This file is saved in a memory card 167, with memory interface 166 managing the flow of data between the memory card and the digital video processing engine.

Referring to FIG. 6, a plurality of control switches located on the exterior of the instrument housing 44 includes a POWER ON/OFF switch 98, as well as a RECORD/PLAYBACK switch 100 controlling the audio recording and playback features of the camera. A series of indicating lamps are also provided, more specifically a power lamp 102, a ready lamp 103, and a recording lamp 104.

Figure 7:
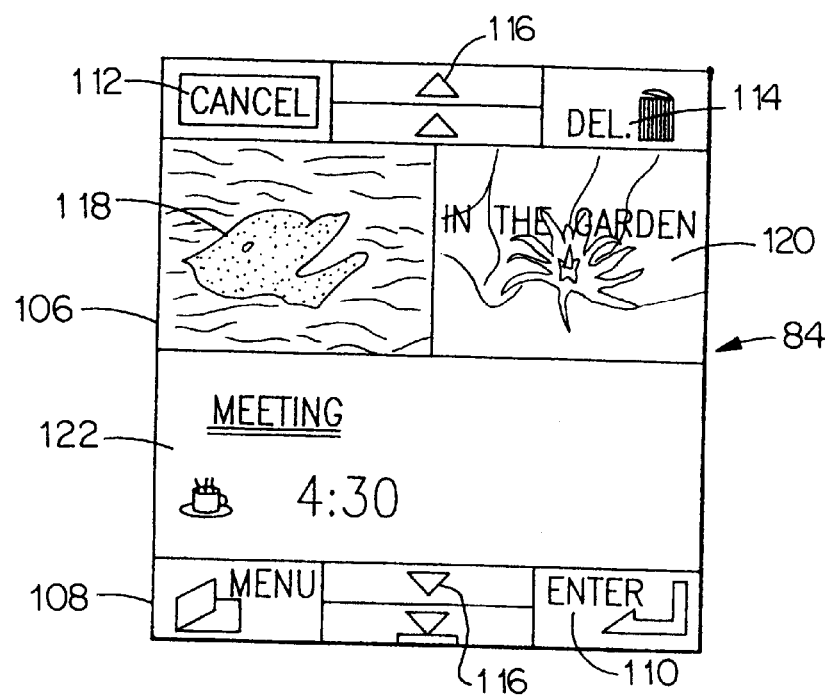
FIG. 7 is a partial rear view of the touch sensitive video display of FIG. 6.

Referring briefly to FIG. 7, the TFT display 84 according to the present device includes a main window 106 and a plurality of selectable keys disposed about the periphery thereof, including a key for accessing a main menu 108, an ENTER key 110, a CANCEL key 112, and a DELETE key 114. Keys 116 are also provided to allow scrolling in either vertical direction. The main window 106 can be selectively divided into separate image fields for allowing multiple stored digital images to be displayed simultaneously, and to allow annotation relating to a displayed image (s). Exemplary image fields 118 and 120 and an annotation field 122 are shown in FIG. 7, though preferably the programmable architecture of the digital video processing engine 78, FIG. 8, allows literally any number of separate fields to be made available. For example, a plurality of miniature captured images (not shown) can be displayed in a sequential manner as a slide show presentation on the main window 106. A stylus pen (not shown) selectively allows notes to be added in the illustrated annotation field 122. The notes are also stored into the internal memory card 167.

The described digital camera used as the diagnostic instrument 42 includes other salient and specific features relating to image capture, such as programmed auto-exposure control, including an electronic single-frame shutter and automatic gain control. The specific teachings of these features do not specifically form a part of the present invention. Therefore, no further discussion is required.

Figure 5:
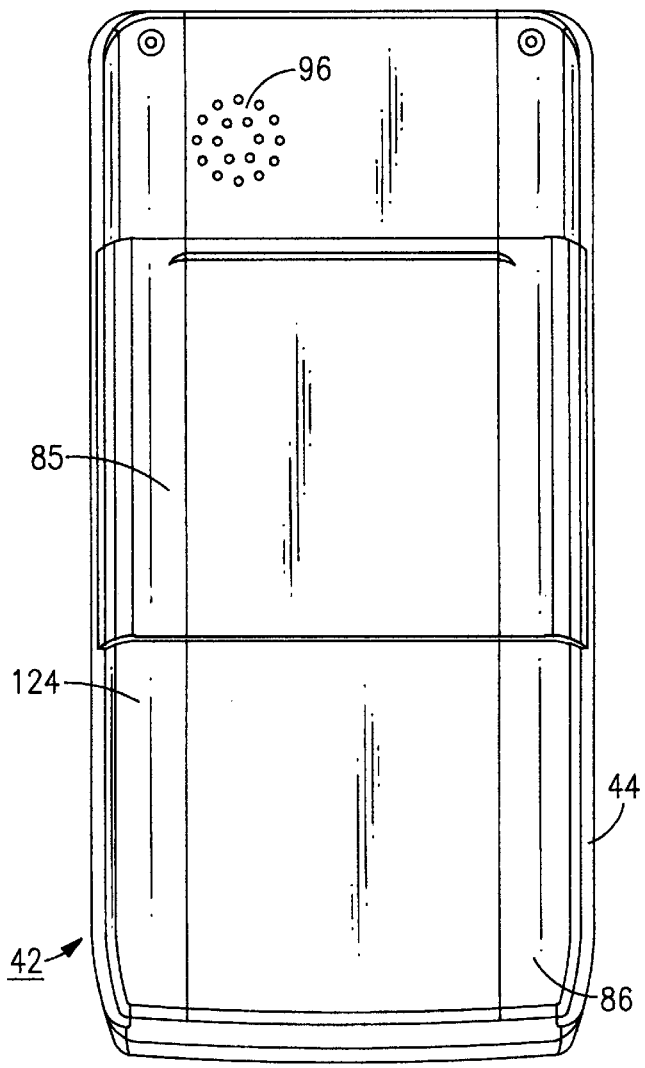
FIG. 5 is a rear elevational view of the multimedia instrument of FIGS. 2–4

Preferably, the instrument housing 44 includes a compartment 124, FIG. 5, accessible from the rear side 86 thereof for retaining a set of rechargeable batteries (not shown) for powering the instrument 42. Alternately, a separate adapter cord (not shown) can supply power from a suitable AC outlet (not shown).

Referring to FIGS. 2–7 and in use, one of the instrument heads is attached to the front interface 48, aligning the optics of the instrument head with the imaging element 72. Activation of the diagnostic instrument 42 using POWER ON switch 98 activates the imaging element 72 and processing circuitry so as to allow a real time video image to be viewed on the TFT display 84. The viewed image can be selectively captured using a shutter release button (not shown) provided on the instrument housing 44 (not shown), causing the image to be stored into the memory card 167, FIG. 8. Activation of the switch 100 allows the microphone 94 to be enabled to allow audio data to be captured corresponding to the video image which is being currently displayed. The instrument 42 includes a MENU feature controlled by the audio processor 148, FIG. 8, which allows the length of the sound clip to be controlled. Alternately, other modes are provided for recording sound without use of the video capture mechanisms, if desired. Audio data is stored in a WAV format, though other formats with varying degrees of compression may also be used. In the present embodiment, approximately 17 minutes of sound data memory are provided though this quantity can easily be varied.

Preferably, the programmable architecture of the digital video processing engine 78 of the presently described instrument 42 also includes an internal calendar, including a date and time stamp, which automatically provides an entry which is stored with each corresponding video and/or audio image captured.

Image data in memory card 167 are stored in the presently described instrument 42 using JPEG compression to reduce the amount of memory they consume. Image quality can be enhanced by adjusting a menu setting in order to produce either high quality photographs or normal (compressed) photographs which increases the compression ratio and reduces the amount of memory needed to store each photograph. In the described camera, the high quality mode allows 66 images to be stored using a compression ratio of 10:1 and 132 photographs to be stored using a compression of 20:1 in the normal mode.

As described in greater detail below, the present multimedia instrument 42 includes a serial, SCSI or other form of data transfer port so as to allow selective interconnection to a computer or more preferably to a docking station or cradle 126, FIG. 9, which is similarly inked to a local PC site 190, FIG. 9, or PC network. Alternately, the stored data (video, annotative, audio, control, etc) can also be transmitted to a video printer, or other suitable peripheral device. Data can also be transferred from the instrument 42 by removing and/or reinserting the memory card 167, as needed.

As noted, FIGS. 2–7 relate to a particular multimedia instrument 42 useful for the present embodiment. The digital camera depicted in the present embodiment is a "COOLPIX 300" sold by the Nikon Corporation, though it will be apparent that other known compact digital cameras, such as the Kodak DC-260, manufactured and sold by the Eastman Kodak Company, or any digital camera having similar or other features can be similarly configured for use in the described diagnostic instrument system.

Reference is now made to FIG. 8 which depicts a more generalized architecture of a multimedia instrument in accordance with the present invention. The digital video processing engine 78 forms the central hub of the instrument which is interconnected to a series of modules, including an imaging module 130, an audio module 140, a video/display module 150, a communications interface module 160 and an illumination control module 170. The imaging module 130 includes at least one lens element, shown diagrammatically as 132, which can be located in the instrument and/or instrument head and is aligned with the electronic imager 133 used for directing an optical signal to an electrical signal through a correlated double sampler (CDS) 134 and an A/D converter 136 for creating a digital signal which is stored into the buffer memory of the digital video processing engine 78 using a timing generator 138 to control shuttering and signal transfer from the imager 133.

The audio module 140 includes a microphone 142 and speaker 144, each interconnected through appropriate converters 146 to an audio processor 148 which is tied by known means to the digital video processing engine 78, which includes logic to correspond audio data with video data from the imaging module 130 for storage.

The video/display module 150 allows display of videoized output provided through a composite video generator 152 to either a local TFT or eyepiece display 154 or to an external video monitor 156. All of the above data can be uploaded or data can be downloaded to the instrument through the communications interface module 160, such as through use of RS232, USB, or a serial port 163, 161, and 162 respectively. Other data, such as vital statistics (patient 1D, height, weight, age, etc) can be directly input through a keypad 164, if provided, while other data, such as analog or digital data from a separate medical instrument, operating instructions, scripts, and the like can also be selectively added or extracted using a memory interface 166, including memory cards 167. Original instructions or protocols can be tied into the digital video processing engine's processor (not shown) through embedded programming 172.

The illumination control module 170 can be tied through the latching mechanism in the previously incorporated U.S. Ser. No. 09/052,570 now U.S. Pat. No. 6,106,457 to the individual instrument heads to the power source 174 (batteries, AC, or other) or a separate illumination control can be provided.

DATA MANAGEMENT SYSTEM

Figure 9:
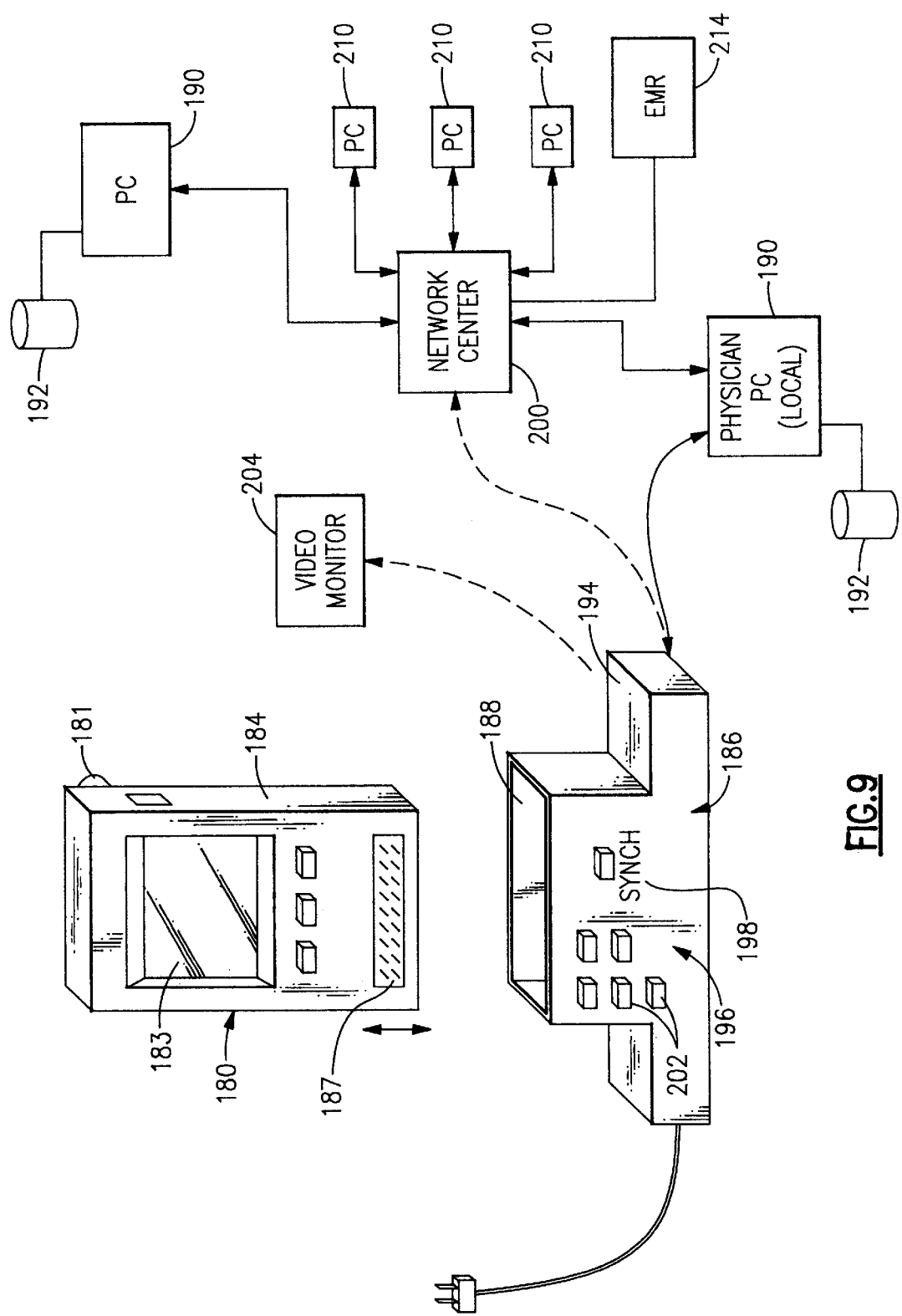
FIG. 9 is a systematic diagram of an examination instrument as used with a receiving cradle capable of transferring data between the diagnostic instrument and a central data network.

With the background of the examination instrument portion of the above system completed, reference is now made to FIG. 9 which illustrate a schematic diagram of a portion of a preferred embodiment of a data/records management system in accordance with the present invention. In brief, a diagnostic instrument 180, similar to the instrument 42 described above, and including the multimedia features of FIG. 8, used in conjunction with a receiving cradle 186 to facilitate data transfer in order to allow uploading of audio, video and other stored data. The cradle 186 is interconnected to a local computer station or site 190, such as found in a physician's office, which incorporates the uploaded data into a local database 192. In the described embodiment, audio (WAV) files are arranged with corresponding video and other stored data in a template which forms the basis for a patient record data sheet, such as shown in FIG. 18, the individual files being separated by identifiers (for example, patient and doctor names) as described in greater detail below.

The instrument 180 includes a housing 184 having an integral display 183 and an interface 181 which uses a plurality of selectively interchangeable instrument heads (not shown in this view) like those previously referred to in FIG. 2. As in the preceding, each of the instrument heads (not shown) includes a specific optical system allowing an optical image of interest to be focused onto a contained electronic imaging element. Support electronics (not shown) converts the optical signal into a captured video signal which is displayed on display 183. A microprocessor (not shown) contains programmable logic which allows a real-time image to be continuously displayed and also allows a predetermined number of images to be captured and stored into memory, selectively or otherwise, along with corresponding audio and/or annotation data added using an integral microphone. The display 183, which is preferably touch-sensitive includes a number of controls on the instrument housing 184 and keys (not shown) as previously described. In another embodiment, the instrument 180 can selectively utilize data, such as to combine audio and annotative data, without reliance on video data for those applications which do not necessarily require this form of input.

In brief, the data files are transmitted from the local computer station 190 (though alternately data could conceivably be transferred directly to the cradle 186) to a network center 200 which includes a number of remote computer stations 210 to which audio data is sent for transcription. The computer stations 210 each utilize human transcriptionists and/or voice recognition software to create a transcription record which is uploaded back to the local computer station 190 in the generated template format. Reports can then be generated which can be stored in the local database 190 in the generated template format, and subsequently printed or transferred, such as to a CPR (Computerized Patient Record) 214 The system in general therefore can create, maintain and update patient files automatically with the files containing several different forms of data.

Still referring to FIG. 9, and according to this specific embodiment, the instrument 180 includes a pinned data exchange SCSI or other connector 187 configured for engagement with a corresponding port (not shown) located in a receiving cavity 188 of the cradle 186. As should be apparent, the form of data transfer is not critical, for example, the data exchange connector can also be USB or serial, as previously shown in FIG. 8.

As shown in FIG. 9, the cradle 186 includes a supporting base portion 194 having the receiving cavity 188 appropriately sized for retaining the lower portion of the diagnostic instrument housing 184, shown partially. Preferably, the base portion 194 can also include a separate storage cavity (not shown) or other means for retaining any of the loose interchangeable instrument heads.

A control section 196 of the cradle 186 includes a synch button or switch 198, as well as a plurality of indicator lamps 202 which indicate specific operational features of the cradle 186, such as to indicate the charging status of the instrument batteries, the status of data transfer, and overall powering of the docking station. For purposes of the present discussion, and upon proper attachment, activation of the synch button 198 causes all audio, control, annotated and video data to be automatically uploaded to the local PC site 190.

The cradle 186 according to the present embodiment is capable of performing additional functions. For example, means are provided for recharging the batteries contained in a battery compartment (not shown) of the instrument 180 while nested. Additionally, the instrument 180 can also be powered (for example, when battery power is low) while attached to the cradle 186, through interconnection to a wall outlet or other source of electrical power. The control section 196 can also be configured with additional switches (not shown) which interconnect with the controller through the data transfer connector of the instrument 180 to allow the instrument to be operated directly from the cradle 186. An advantage realized by this form of control is that the instrument 180 can be made capable of receiving data from other instruments, such as a clinical vital signs monitor, for storage as part of a patient protocol.

Still referring to FIG. 9, the cradle 186 also preferably allows connection to a separate video monitor 204 or other peripheral device for viewing of the captured images, such as with other doctors, patients or interested parties. Alternately, the instrument 180, also allows direct connection to the video monitor 204 without requiring direct use of a cradle 186, if desired. Corresponding audio and annotation data can be similarly transferred with the video data in a manner known in the field.

Figure 10:
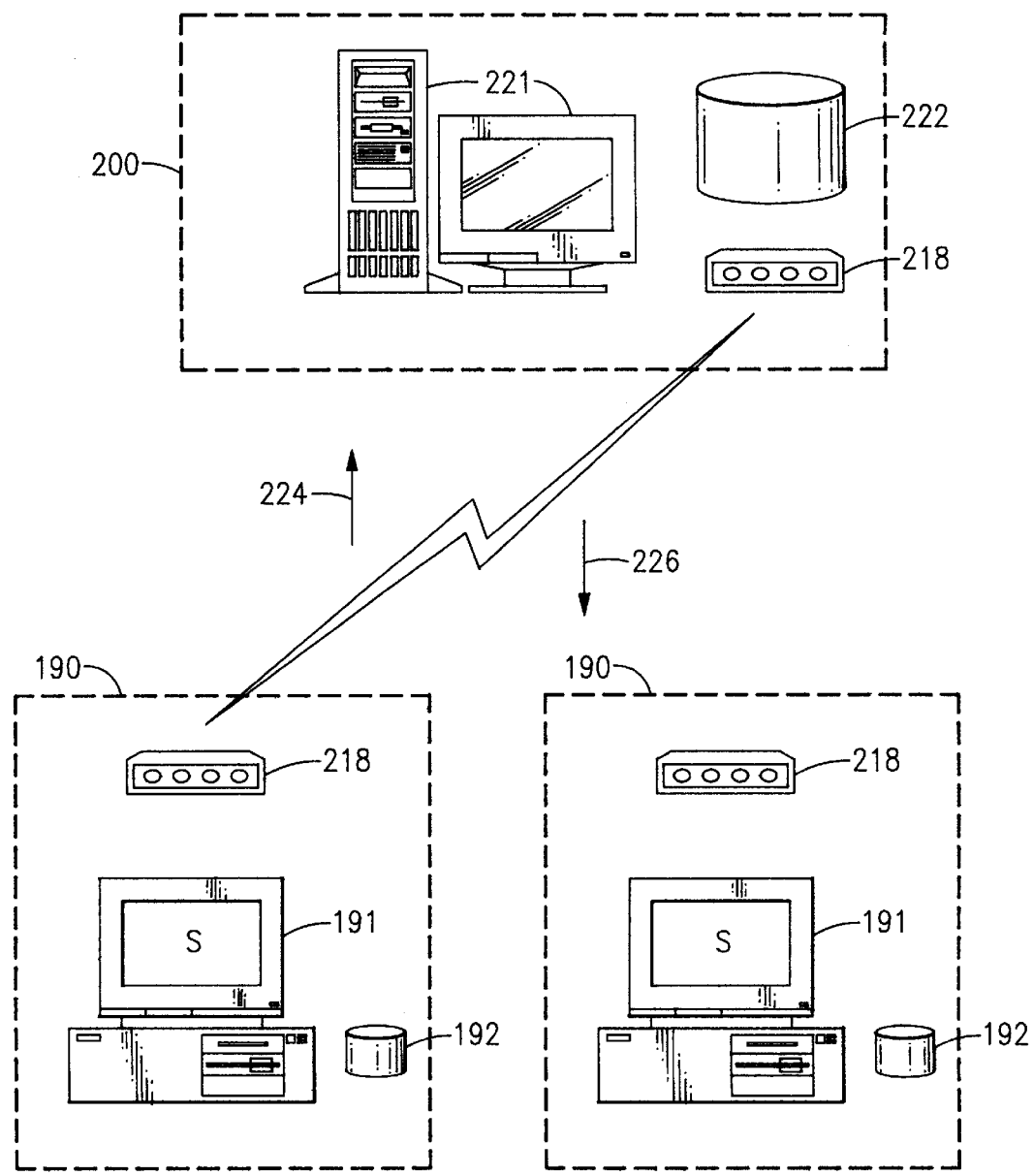
FIG. 10 is a schematic diagram showing a portion of the data management system and in particular data transfer between a network center and local PC stations.

FIG. 10 illustrates the general relationship between the network center 200 and individual local PC sites 190. The network center 200 includes a central server 191 which is tied remotely through telephone lines using respective modems 218 to any number of identified local sites 190. Each of the local PC sites 190 include storage capacity in the form of the local database 192 which allows data to be uploaded and downloaded relative to a central relational database 222, see arrows 224 and 226.

Figure 11:
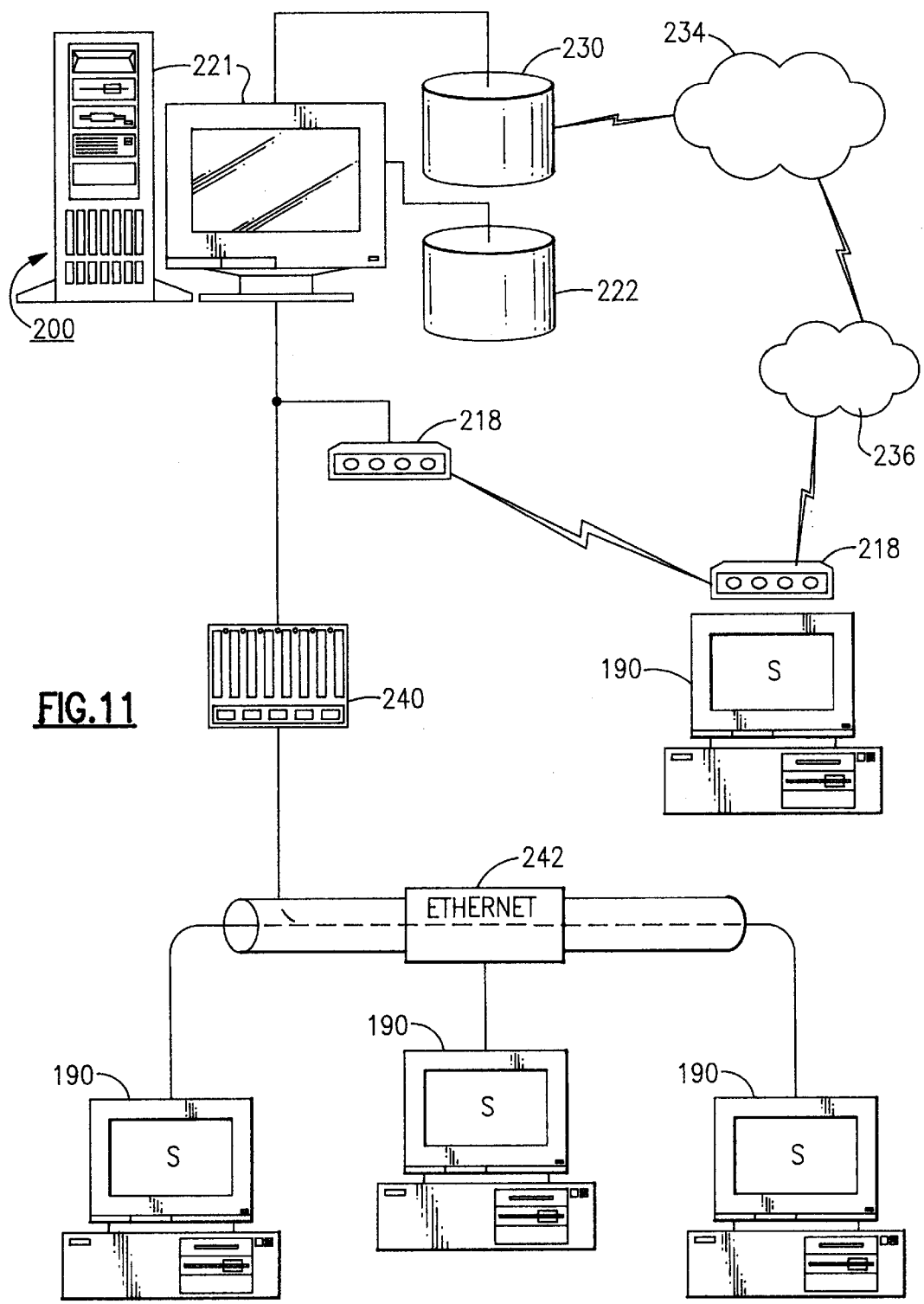
FIG. 11 is a schematic diagram of the portion of the data management system of FIG. 10 illustrating multiple alternate forms of data transfer between the local PC stations and the network center as contemplated by the present invention.
Figure 12:
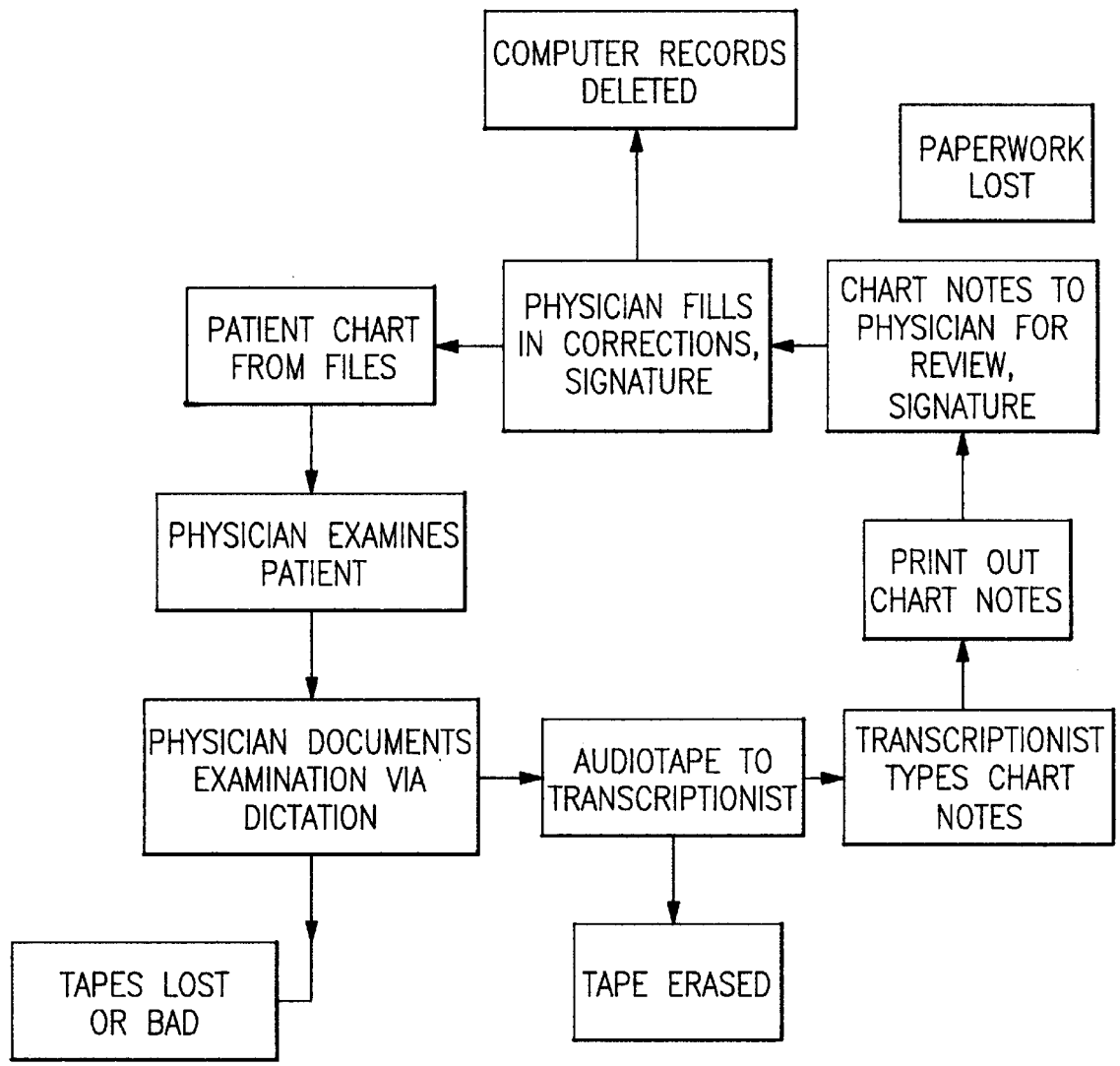
FIGS. 12 and 13 are flow charts representative of prior art methodology pertaining to transcription of audio medical records.
Figure 13:
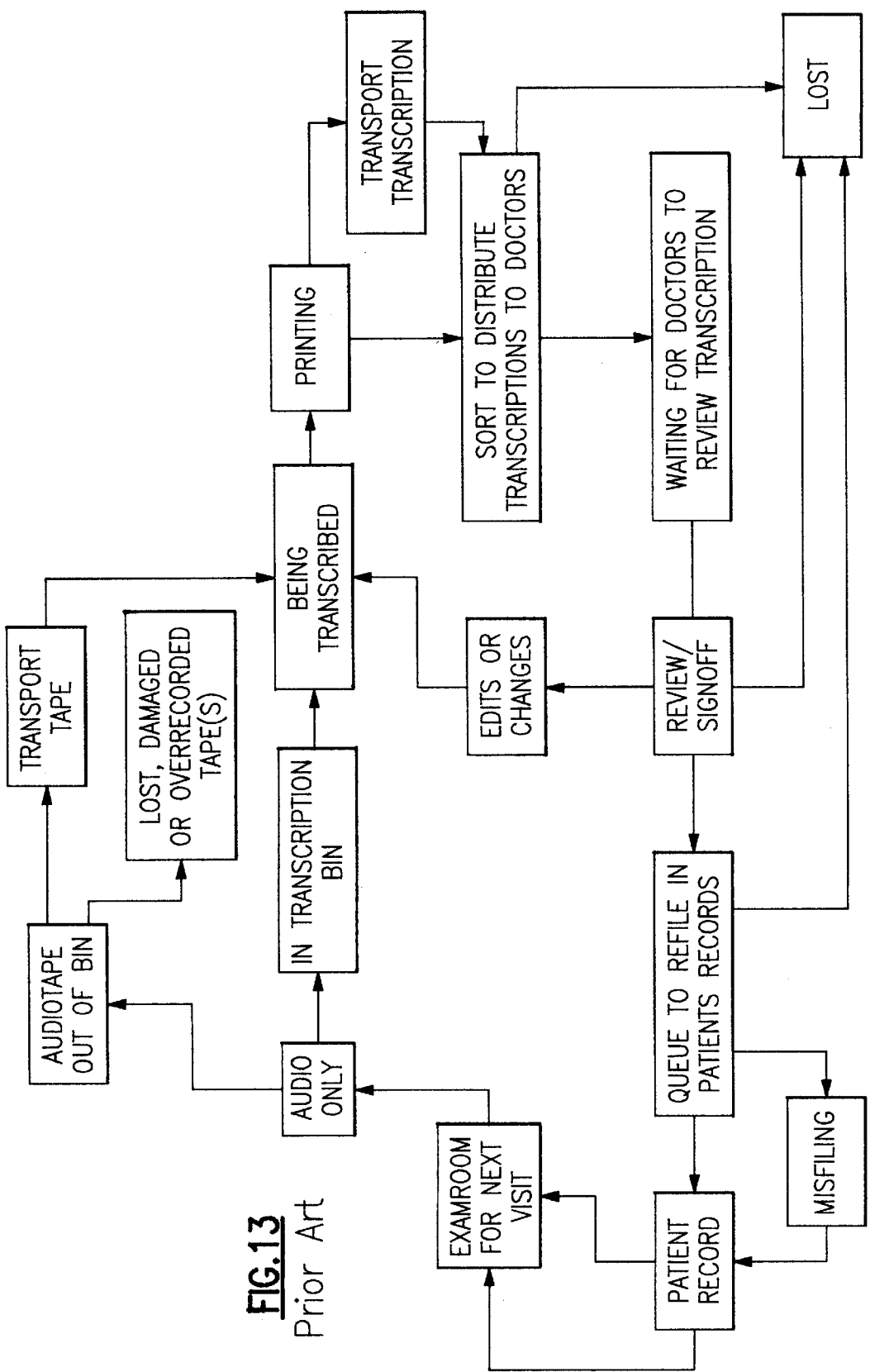
Figure 17:
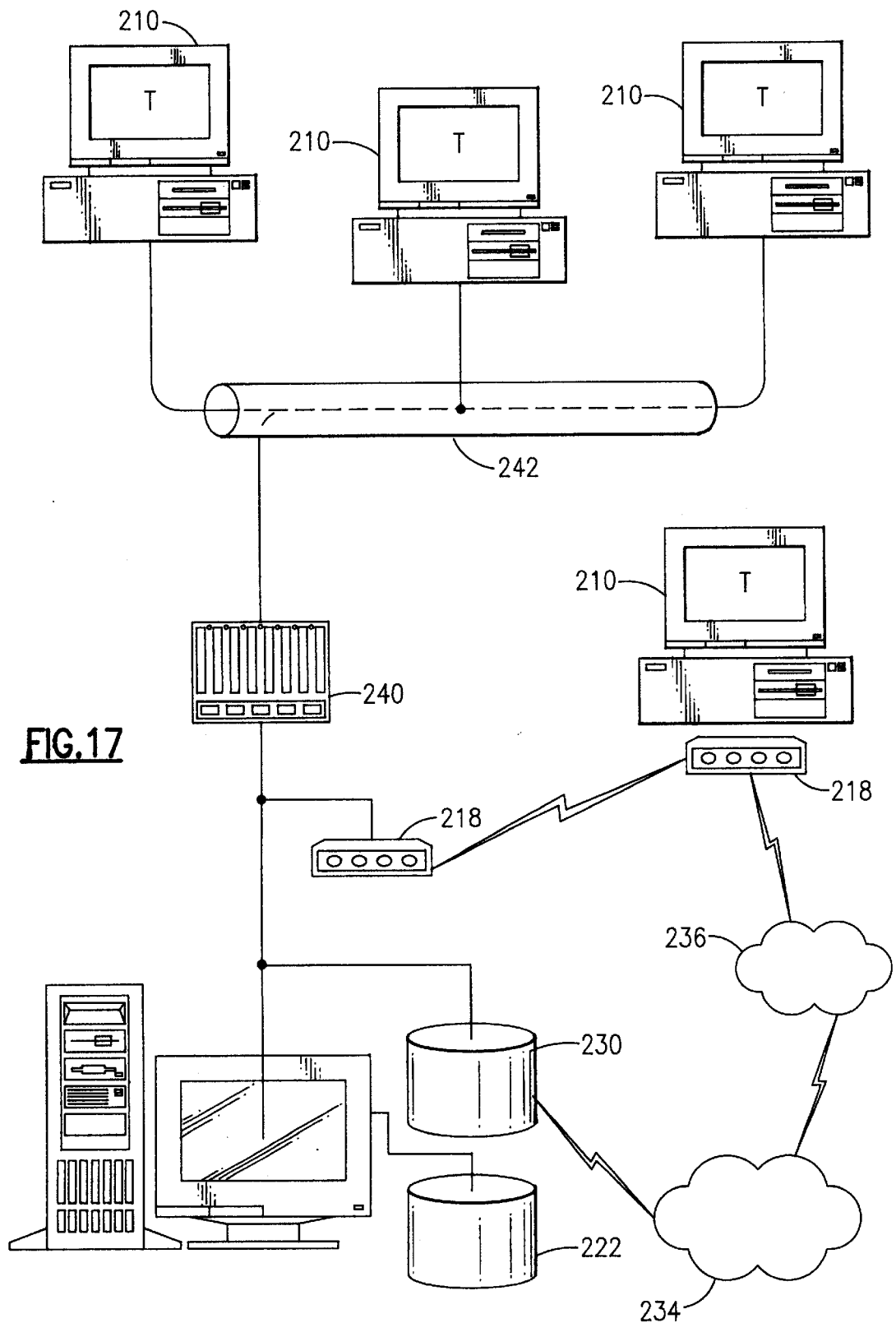
FIG. 17 is a schematic chart illustrating multiple alternate forms of data transfer between remote transcription sites and the network center for the data management system of FIGS. 10, 11, and 14–16.

FIG. 11 illustrates alternate forms of data transfer between the network center 200 and the local physician's PC sites 190. In one preferred method, the individual sites 190 are connected into the network center 200 using LAN server connections using a hub 240, each being interconnected using Ethernet 242. In another alternate version, the network center 200 can be interconnected to one or more of the sites 190 via telephone lines using respective modems 218. Finally, the network center 200 can include a web-related database 230 accessible over the Internet, shown schematically as 234 using an Internet Source Provider (ISP), shown as 236. Similar transfer is possible as shown in the embodiment described below between the remote transcription sites 210 and the network center 200 according to FIG. 17.

Figure 14:
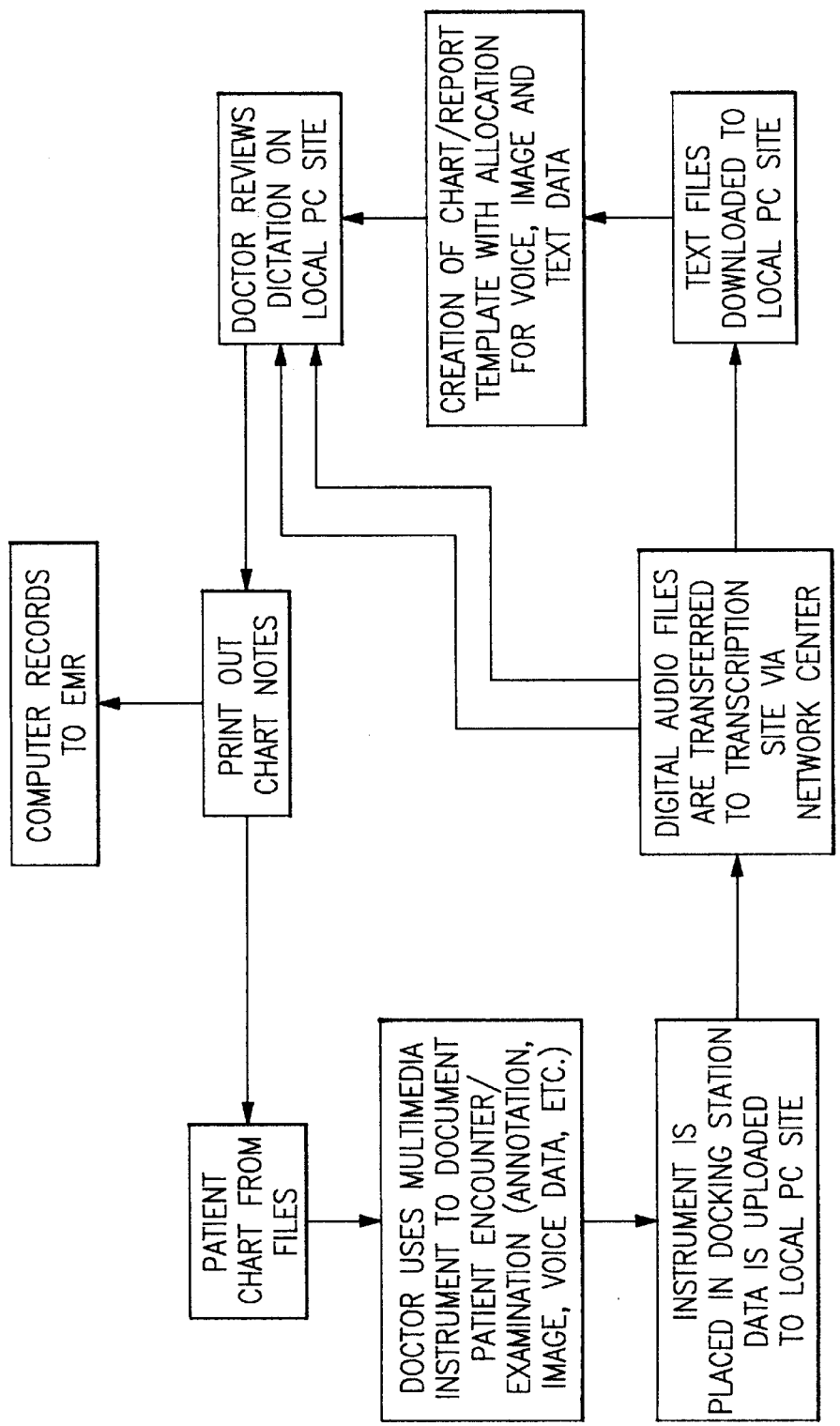
FIG. 14 is a simplified flow chart of a transcription/report aspect of the data management system of FIGS. 10 and 11.
Figure 15:
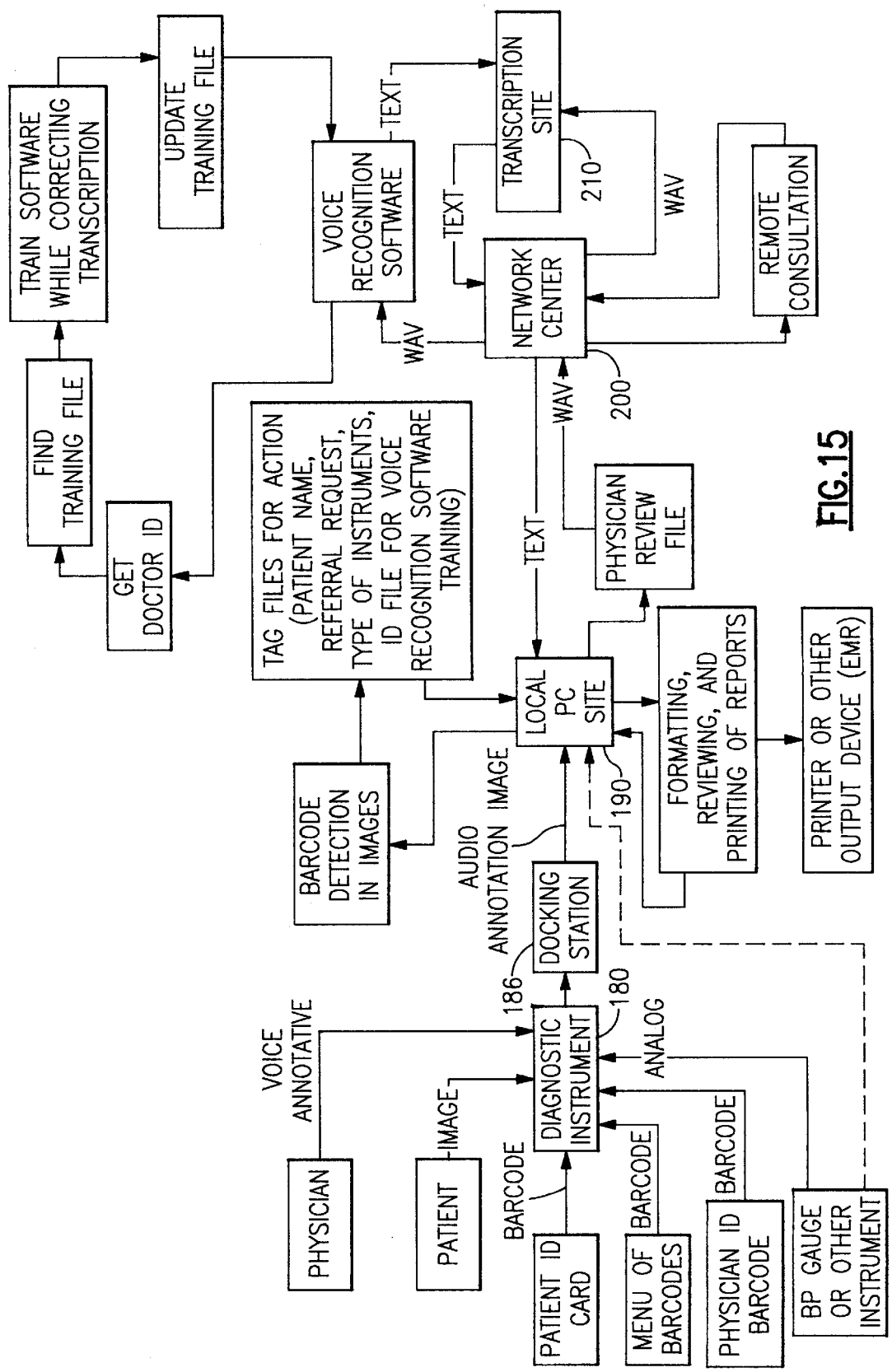
FIG. 15 is an enhanced diagrammatic view of a transcription/report transcription procedure of FIG. 14.
Figure 16B:
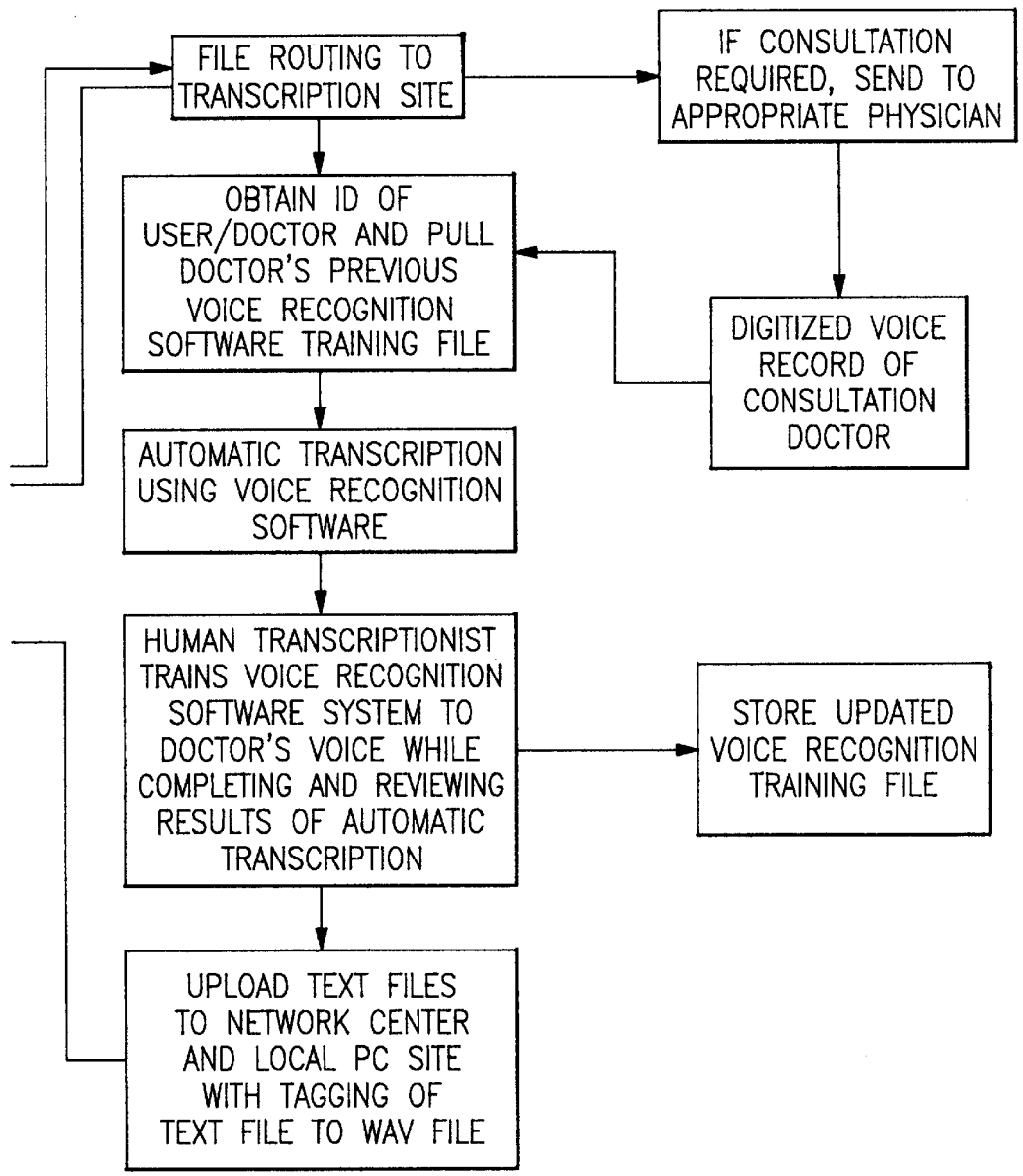
FIG. 16 is a flow chart of a patient encounter utilizing the data management system of FIG. 15.

FIGS. 14–16 are flowcharts presenting the sequence of steps used in obtaining data, transferring data to a local PC site 190, for uploading stored data to the network center 200, for further uploading audio files to a remote transcription site and for obtaining transcription textual data which can be incorporated into a finalized patient report. More particularly, FIG. 14 is a generalized flowchart of the procedure. FIG. 15 is a diagrammatic representation indicating data transfer between the diagnostic instrument 180, the docking station (receiving cradle) 186, the local PC site 190, the network center 200 and the remote transcription site 210, and FIG. 16 is an enhanced flowchart of the one shown in FIG. 14 which relates to the flow of data between the examination room where the instrument is first used, the doctor's office in which the local PC site 190 is located, the network center 200 and remote transcription sites 210 and finally a consulting physician's office 250 in which consultation data in the form of audio may also be transcribed and incorporated into a patient record.

The preferred record management system is herein described with reference to each of FIGS. 14–16. The description relates specifically to an office visit by a patient, though it will be readily apparent that the above could also apply to a typical round or hospital shift or other suitable setting in which a single patient or plurality of patients are to be examined.

Initially, the patient chart is pulled from the files for the physician. A scripted set of instructions are preferably loaded into the instrument for initializing and using the instrument 180 with a plurality of patients. A unique ID code is assigned, both to the user (the physician) and to the instrument 180 for allowing data to be uniquely uploaded and downloaded to the local database 192 and/or central database 222. After loading the user ID, the instrument ID is preferably encoded automatically and the physician then initiates the examination by utilizing the diagnostic instrument 180 by removing the instrument from the cradle 186 and attaching the general purpose instrument head 52, FIG. 2, to the front interface 48 of the instrument in the manner described previously. Preferably, the cradle 186 recharges the batteries of the instrument 180 sufficiently to allow several hours of typical use.

Depending on the particular protocol of the local database 192 (that is, the template of the patient data folder created by the database), a patient ID and doctor ID are first captured. One way of obtaining either ID is by capturing and storing video image(s) of the printed patient chart. The ID may or may not include bar code information. Alternately, a video image of the patient can be taken and the appropriate data can be added via annotation, using the TFT display 183. According to another alternate embodiment, doctor and patient information can be captured via a menu in the microprocessor software. In yet another alternate manner, the physician could enter all patient data into folders loaded on the instrument 180, using data entered from the local PC 190. Each technique is diagrammatically in FIG. 15. As in the preceding, images are captured and stored by first activating the instrument 180 framing the image to be captured into memory in the integral display 84. Actuation of the shutter control button (not shown) of the instrument 180 allows each digital image of interest to be stored into the buffer memory of the digital video processing engine 78, FIG. 8. Vital sign and other pertinent patient data would also be added, either as a captured video image or be entering the data directly into the internal memory of the instrument. Data from other instruments or from other measurements can be entered into the instrument 180 by a number of known methods. For example, data could be sent using RF or other wireless technologies. Data could also be entered using the keyboard of the local PC site 190, through buttons, or other known input devices on the instrument itself.

The physician is then ready to begin examinations, such as done on a daily basis in the office, for example. As described above, each patient visit is initialized by capturing a video image of the patient ID and storing the image into the internal memory of the microprocessor 78, FIG. 8. Additional patient data can then be captured using the instrument and selectively any of the interchangeable instrument heads which may be required. The physician can also capture audio data pertaining to each captured video image of interest using the microphone 142, FIG. 8, the video and audio data being available for playback using speaker 144, FIG. 8 or annotative data using the TFT display 183 at any point during the examination. The instrument 180 according to the present embodiment utilizes an internal calendar with date stamping to identify the date and time of each captured image. Alternately, this data could be entered separately or other data could be entered, such as from an external source, including operating instructions, protocol, height and weight data, as well as other pertinent information which can be added using the local computer or the network, for example. Each new patient requires identification of the new patient ID, as described above. During the exam, after the exam, after examining several patients, or at the end of the day, the physician can perform his dictation in the usual manner. At the end of the day, or after a determinate number of examinations, the instrument 180 is loaded into the receiving cavity 188 of the cradle 186. The software contained within the instrument 180 further preferably allows additional data entry for an earlier patient, if desired, such as to include later obtained data from another external source, etc.

Upon loading the diagnostic instrument 180 into the receiving cavity 188 of the cradle 186, the synch button 198 is actuated, automatically transferring the stored audio (WAV), video, and annotation data files (if any) to the database 192 of the local PC site 190. The software provided in the local PC site 190 loads the raw data into a specific template, an example of which is shown in FIG. 18. Preferably, a confirmation indication is provided on the display of the local PC 190 to indicate that all images and audio clips have been removed from the instrument 180.

In a particular embodiment, the instrument 180 can also include a counter, preferably stored in the EEPROM 172, FIG. 8, which counts the number of images taken by the instrument. As one means for preventing unauthorized use and/or theft, the counter output can be automatically checked and reset by the software contained in the local database 192 when the instrument 180 is synched thereto. Therefore, if the instrument 180 is not synched in the prescribed manner, then further use of the instrument would be disabled. In this manner, unauthorized persons could not access the instrument and, for example, take pictures.

During the data transfer to the local database 192, the doctor and patient IDs are first located and identified. In the case of use of bar codes, the local PC site 190 preferably includes recognition software which allows identification of the doctor and patient IDs and loads the data into an already existing or newly created patient file. Most preferably, the software includes pattern recognition or bar code recognition programs which can detect the existence of a bar code or other pattern from an existing and captured video image and then decode the bar code or pattern if such information is present. In the present embodiment, the doctor ID or the patient ID may contain a 1D or 2D bar code pattern, the determination of which engages the following transcription routine. Details relating to the software for detecting bar code from a digitally captured video image is described in greater detail in U.S. Ser. No. 08/964,341 filed Nov. 4, 1997, the entire contents of which are herein incorporated by reference. The bar code recognition software can also be used to control the instrument 180. For example, the software can be used to indicate the type of instrument head being used or which anatomy type a physician is examining or imaging.

Upon identifying the doctor and patient, the software creates a new data folder in the event of a previously unlisted patient, or accesses an already existing patient folder by comparison to a list stored in memory. Preferably, a security feature is loaded into the logic of the local PC site 190 prompting a user identification window and requiring a password be entered prior to allowing access to the raw data for review or prior to transferring the data to the network center 200. The software automatically stores images and other associated data input to a tagged file having the ID number or name attributed to it. As such, the files can be automatically stored without requiring human intervention or assistance. In addition, the files can also be tagged for action, such as additional tests, follow-up visits, inoculations, prescriptions, or other procedures.

After all of the stored data (video, audio, etc.) has been downloaded onto the local database 192 and reviewed, an election is made to send all or part of the data, in this embodiment the digital audio files (WAV) files, such as through phone lines as part of a LAN connection, by dial-up networking, e-mail transfer or alternately over the Internet by known means to the network center 200. Prior to transmitting this data, the WAV files are first previewed, such as by the physician at the local PC site 190, if desired by selection of the appropriate entry queued at the patient template. Alternately, other image data can be archived to the database 222 of the network center 200 while the audio data is being transmitted.

Preferably, the local PC 190 encrypts the data prior to transferring the data to the network center 200, where the data will be decrypted using techniques known in the field. The details of encryption/decryption do not form an essential part of the present invention and therefore require no further discussion. The data is transferred between the local PC site 190 and the network center 200 using the template originally created at the local PC site. Because the data is transferred in this format, it is not necessary to send the corresponding video data to the network center 200. However, image files may be transferred for data storage (warehousing) in the central database 222 or for sending referring letters via e-mail or other purposes.

At the network center 200, the audio digital (WAV) files can be transcribed after being loaded into a server or other hardware, the center having a plurality of linked computer stations 210 using human transcriptionists in combination with an automatic voice recognition (hereinafter referred to as VR) software system, such as Dragon Systems Naturally Speaking to develop a database of a doctor's vocabulary. Preferably, the VR software contains an adaptation or learning mode which improves the general efficiency of transcription as related to specific physician(s). That is, as the number of transcriptions using the dedicated physician necessarily improves more efficiently over time by updating of a specific dedicated physician file. However, unlike traditional uses of voice recognition software, the training would be done by transcriptionists rather than the speakers themselves.

Upon receipt of the raw audio data from the local PC site 190, the physician's ID is retrieved from memory at the central database 222 and the training file (if existing) is accessed. Otherwise, a new doctor's training file is created. An original version of the transcription is then automatically created, the results of which are then subsequently transmitted, also automatically, to a separate PC site 210 for review by a human transcriptionist.

Using the WAV files obtained from memory by accessing the training folder, the transcriptionist can effect any changes which may be required based on a review of the created transcription, the changes being directly inputted into the record and also into the VR software into the training file. The above procedure can then be iterated until the training using the VR software has progressed to a given level and a suitable transcription is produced. The number of iterations (edits) will significantly decrease with an increasing number of transcription files, based on the learning mode, and assuming the physician performs an initial vocabulary building exercise typically required of presently known VR software. This improvement creates an increase in efficiency and accuracy after an initial learning curve for each physician. At the transcription site 210, the transcriptionist can also access the video and annotation files, if transmitted and as needed, to further improve the reviewing process. The chief benefit of this sort of training method is that the difficult job of training VR software is done by lower paid personnel which is more efficient, thereby freeing the physicians to perform the jobs they were trained for.

Following the transcription procedure at the network center 200, a copy of the transcription is removed from the training file and is attached to the specific patient data file in the appropriate location prompted by the incoming template. The data file is then transferred to the local PC site 190 in the template format having the transcribed information added as shown in FIG. 18 in the vicinity of the corresponding video image. As in the preceding, data transfer is performed through connections as shown in FIG. 11. At the local PC site 190, the transcription can then be reviewed by the physician where the information can be reviewed and edited for accuracy and additional editing, if needed. The physician can also access the image and audio portions of the patient chart from the local database 192, if needed, while reviewing the transcription. A finalized copy can be printed and approved or signed off by the physician prior to adding a hardcopy of the file to the patient record.

The appropriate files are originally combined using a data file accumulated prior to transcription which is presented using a script template. The template can be reviewed and the audio information can be accessed by cursor, mouse or keyboard control to icons presented adjacent to the video images. The icons access the audio files with the annotation files being presented along with the video files. After the transcription has been completed, a hardcopy with the transcription record added appropriately with the images in place of the icons can be printed for placing in the patient file.

The video images, once received into the system are scanned. Subsequent changes, such as cropping or airbrushing, etc may be detected to prevent distortion or falsification of records. Any annotations, graphical or text, will be stored as a separate file and non-destructively overlaid on the image for viewing purposes. Further, the system preferably contains appropriate encryption programs for preventing access to the records by unauthorized persons.

The data can also be transmitted over the telephone lines in any known manner or via the Internet to an EMR 214 or other remote site, with the network center 200 also allowing receipt of information therefrom from other sources, etc. to aid in networking. For example, information from an instrument at a remote site relative to the local PC site 190 can be transmitted into the local database 192 or be unlinked by known means through the cradle 186 to the instrument 180.

Though the preceding data management system described in detail, a technique of remotely transcribing using a central bank of computers, it should be realized that the transcription could certainly be done locally. That is to say, the immediate benefit is the ability of the instrument of the present invention to incorporate multiple forms of data which can be linked, including audio, video, annotation, etc., to allow data management to be better coordinated. The features, though pertaining to the medical profession in the preceding embodiment, are clearly applicable to other service providers, including attorneys, insurance agents, and the like, as well as a myriad of other suitable applications.

PARTS LIST FOR FIGS. 1–18

- 10 diagnostic instrument system
- 14 medical instrument
- 16 elongate body
- 17 proximal-end instrument
- 18 distal-end instrument
- 20 hand section
- 22 sheathed cable
- 24 proximal end-handle section
- 28 video processing module
- 29 cavity
- 30 control panel
- 32 light/power box
- 34 video monitor
- 40 diagnostic instrument system
- 42 multimedia diagnostic instrument
- 44 housing
- 48 front interface
- 52 general purpose viewing head
- 56 dermatological instrument head
- 60 high magnification instrument head
- 64 otological instrument head
- 68 interior
- 70 latching member
- 72 electronic imaging element
- 74 ears
- 76 window
- 78 digital video processing engine
- 80 contacts
- 82 contacts
- 84 display
- 85 sliding cover
- 86 rear side housing
- 90 axis housing
- 93 viewing axis
- 94 microphone
- 96 speaker
- 98 POWER ON/OFF switch
- 100 RECORD/PLAYBACK switch
- 102 power lamp
- 103 ready lamp
- 104 recording lamp
- 106 main window
- 108 MENU key
- 110 ENTER key
- 112 CANCEL key
- 114 DELETE key
- 116 scroll keys
- 118 image field
- 120 image field
- 122 annotation field
- 124 battery compartment
- 130 imaging module
- 132 lens
- 134 CDS
- 136 A/D converter
- 138 timing generator
- 140 audio module
- 142 microphone
- 144 speaker
- 146 converters
- 148 audio processor
- 150 video/display module 152 composite video generator
154 video monitor-external
160 communications interface module
162 serial port
164 keypad
166 memory interface
170 illumination control module
172 embedded program storage
180 multimedia instrument
181 interface
183 display
184 housing
186 receiving cradle (docking station)
187 data exchange pinned connector
188 receiving cavity
190 local site
191 PC
192 local database
194 supporting base portion
196 control section
198 synch button
200 network center
202 indicator lamps
204 external video monitor
206 remote PC
208 database
210 remote transcription stations
214 MR
218 modem
220 mainframe computer
222 central relational database
224 arrow
226 arrow
230 web relational database
234 Internet
236 Isp
240 hub
242 Ethernet

We claim:

1. A method for creating and maintaining records containing at least image, text and audio data during a physician's office encounter said method comprising the steps of:

attaching at least one medical diagnostic instrument head including at least one of a otoscopic, episcopic and ophthalmoscopic instrument head to a hand-held digital camera thereby creating a hand-held medical multimedia instrument;

capturing image data relating to at least one medical target of a patient using said hand-held medical multimedia instrument;

capturing audio data corresponding to at least one patient using said hand-held medical multimedia instrument;

capturing control data relating to at least captured image and audio data using said hand-held multimedia instrument;

transferring the captured audio, control and image data from said multimedia instrument to at least one of a local and remote computer station;

storing said data in a database associated with said computer station;

transferring audio data from said computer station to at least one transcription site;

transcribing said audio data at said at least one transcription site into text-readable data;

transferring said text-readable data from said at least one transcription site to said computer database for storage thereof; wherein said transferring step includes the further step of incorporating said text-readable data with associated image, control and audio data as part of a patient specific data record.

2. A method according to claim 1, including a network center having data storage means, said network center being interconnected to a plurality of transcription sites and at least one said computer station, the method including the additional steps of:

transferring stored audio data from said at least one computer station to said network center;

storing the transferred audio data in said data storage means;

transferring said audio data to said at least one transcription site for transcription of said audio data;

creating text-readable data at said at least one transcription site;

transferring said text-readable data to said computer station; and incorporating said text-readable data with associated image and audio data into said patient specific data record in said computer database.

3. A method according to claim 1, wherein said hand-held multimedia instrument includes means for receiving and storing at least one form of data from a number of discrete instruments and annotation means for annotating onto captured image data, wherein said method includes the step of transferring all stored data, including annotation data and received and stored instrument data, to said computer station.

4. A method according to claim 1, wherein said at least one computer station includes identification means for discriminating object recognizable symbols from a captured image, said method including the steps of:

scanning stored images received from hand-held medical multimedia instrument for object symbology;

decoding said symbology if detected by said identification means.

5. A method according to claim 1, including the additional steps of:

initializing at least one patient encounter by creating a data file within data storage means of the digital camera of said medical multimedia instrument;

capturing image, control and audio data relating to said at least one encounter using said multimedia instrument;

transferring all captured data from the data storage means of said hand-held multimedia instrument to said computer station;

storing captured data in said computer database;

converting said stored data of each patient encounter into a separate report template having allocation for all captured data based on said created data file;

transferring audio data to a network center having means for identifying and storing said audio data;

sending identified audio data relating to a user to a transcription site for transcription;

transcribing said identified audio data into text-readable data;

transferring the text-readable data to said network center;

transferring the text-readable data to said computer station; and incorporating said text-readable data into the corresponding report template.

6. A method according to claim 5, including the step of adding other patient-related data to said data file prior to transferring said captured data from said hand-held multimedia instrument to said computer station.

7. A method according to claim 4, in which said multimedia instrument includes means for receiving and storing data from a plurality of separate instruments and means for annotating captured image data relating to at least one patient of interest, said computer site having means for storing all transferred data from said medical multimedia instrument into said report template.

8. A data management system for use in a physician office encounter, said system comprising:

at least one hand-held multimedia examination instrument comprising a hand-held digital camera having at least one medical diagnostic instrument head attached thereto, said instrument having imaging means for capturing at least one image of interest, audio recording means for recording audio data relating to said at least one image, control data recording means for capturing data necessary for the management of captured image and audio data, and first data storage means for storing captured image and audio data; and means for transferring audio data between said first data storage means and transcribing means for converting said audio data into text-readable data.

9. A data management system as recited in claim 8, wherein said transferring means includes at least one of a local and remote computer station having second data storage means capable of storing all captured data from said hand-held multimedia examination instrument.

10. A data management system as recited in claim 8, wherein said computer station includes identification means for identifying data files created by said multimedia examination instrument and means for placing said captured data into a report template stored by said second data storage means, and in which said transferring means includes a network center interconnected to said computer station, said network center interconnecting at least one computer station with a plurality of transcription sites, said network center including a computer having centralized data storage means.

11. A system according to claim 8, in which said hand-held multimedia examination instrument includes means for receiving and storing data from discrete instruments and means for annotating captured image data relating to a subject of interest, said computer station having means for storing all data transferred from said hand-held multimedia examination instrument into a corresponding report template.

12. A system according to claim 8, wherein said at least one multimedia examination instrument includes means for securing against theft and unauthorized use, said computer station having means for authenticating control data transferred from said at least one hand-held multimedia examination instrument and for disabling said at least one examination instrument upon detection of an unauthorized use.

13. A system according to claim 12, wherein said at least one multimedia examination instrument includes means for counting the number of images captured, said disabling means being connected with said counting means to disable said instrument after a predetermined number of images have been taken.

14. A system according to claim 9, wherein said transferring means includes means for capturing audio and control data obtained over a telephone line as a second data storage means redundant to said examination instrument, said transferring means further being capable of sending audio and control data needed to identify subjects of said instrument obtained by said second data storage means to said computer station.

15. A system according to claim 9, including template means for forming patient records for retaining stored data from said at least one multimedia examination instrument, said transcription means including means for transferring data to selective fields of selective patient records created by said template means.

16. A system according to claim 9, wherein said transferring means includes means for automatically transferring stored data to a plurality of remote locations for consultation upon transfer of said stored data to said first storage means.

17. A system according to claim 9, wherein said transferring means includes means for transferring stored data between other multimedia examination instruments.

18. A method according to claim 1, including the additional steps of:

transferring at least portions of said patient specific data record to said hand-held multimedia diagnostic instrument; and using said hand-held diagnostic instrument to display at least portions of said patient specific data record.

19. A method according to claim 18, including the additional steps of releasing a first instrument head from said hand-held digital camera following examination of a first area of interest and attaching at least a second instrument head prior to examining at least a second area of interest.

20. A system according to claim 8, wherein said instrument heads are releasably attachable to said hand-held digital camera, said instrument heads including at least one of an otoscopic, episcopic and ophthalmoscopic instrument head.

21. A system according to claim 20, wherein said instrument heads are releasably attachable to said digital camera.

* * * * *